US007214836B2

(12) United States Patent
Brown et al.

(10) Patent No.: US 7,214,836 B2
(45) Date of Patent: May 8, 2007

(54) METHOD OF DECOMPOSING ORGANOPHOSPHORUS COMPOUNDS

(75) Inventors: R. Stanley Brown, Kingston (CA); Alexei A. Neverov, Kingston (CA); Josephine S. W. Tsang, Kingston (CA)

(73) Assignee: Queen's University at Kingston, Kingston, Ontario (CA)

( * ) Notice: Subject to any disclaimer, the term of this patent is extended or adjusted under 35 U.S.C. 154(b) by 0 days.

(21) Appl. No.: 10/798,880

(22) Filed: Mar. 12, 2004

(65) Prior Publication Data

US 2004/0230082 A1 Nov. 18, 2004

Related U.S. Application Data

(60) Provisional application No. 60/453,762, filed on Mar. 12, 2003.

(51) Int. Cl.
*C07C 29/12* (2006.01)

(52) U.S. Cl. .................................................... 568/886

(58) Field of Classification Search ................. 568/886
See application file for complete search history.

(56) References Cited

U.S. PATENT DOCUMENTS

| | | | | |
|---|---|---|---|---|
| 3,079,346 | A * | 2/1963 | Jackson | 510/110 |
| 3,725,269 | A | 4/1973 | Wolverton | |
| 5,859,064 | A | 1/1999 | Cronce | |
| 2004/0096415 | A1* | 5/2004 | Franke et al. | 424/70.22 |

FOREIGN PATENT DOCUMENTS

| | | | |
|---|---|---|---|
| DE | 299458 | | 4/1992 |
| EP | 0906773 | A1 | 4/1999 |
| EP | 0909774 | A1 | 4/1999 |
| WO | WO 96/05208 | | 2/1996 |
| WO | WO 00/48684 | | 8/2000 |
| WO | WO 01/30452 | A1 | 5/2001 |
| WO | WO 02/072206 | A1 * | 9/2002 |

OTHER PUBLICATIONS

Balakrishnan et al., Catalytic pathways in the ethanolysis of fenitrothion, an organophosphorothioate pesticide. A dichotomy in the behaviour of crown/cryptand cation complexing agents, Can. J. Chem. 79, 2001, 157-173.*

(Continued)

*Primary Examiner*—Thurman Page
*Assistant Examiner*—Chukwuma Nwaonicha
(74) *Attorney, Agent, or Firm*—Carol Miernicki Steeg; Stephen J. Scribner

(57) ABSTRACT

Methods and kits for decomposing organophosphorus compounds in non-aqueous media at ambient conditions are described. Insecticides, pesticides, and chemical warfare agents can be quickly decomposed to non-toxic products. The method comprises combining the organophosphorus compound with a non-aqueous solution, preferably an alcohol, comprising metal ions and at least a trace amount of alkoxide ions. In a first preferred embodiment, the metal ion is a lanthanum ion. In a second preferred embodiment, the metal ion is a transition metal.

42 Claims, 10 Drawing Sheets

OTHER PUBLICATIONS

Neverov et al., La3+-Catalyzed Methanolysis of Phosphate Diesters. Remarkable Rate Acceleration of the Methanolysis of Diphenyl Phosphate, Methyl p-Nitrophenyl Phosphate, and Bis(p-nitrophenyl) Phosphate, Inorg. Chem.; (Article); 2001; 40(14); 3588-3595.*

Buncel et al., Alkali metal ion catalysts in nucleophilic displacement by ethoxide ion on p-nitrophenyl phenylphosphonate: Evidence for multiple metal ion catalysis, Can. J. Chem. 81, 2003, 53-63.*

Yang et al., Decontamination of Chemical Warfare Ageints, Chem. Rev., 1992, 82, 1729-1743.*

Platt, Reaction of Lanttanide Nitrates with Dimethylbenzoylphosponate, Polyhedron, 12, No. 5, 467-472, 1993.*

Barr, L., et al., "Metallocyclodextrin Catalysts for Hydrolysis of Phosphate Triesters", *Tet. Lett.*, 43: 7797-7800 (2002).

Bunton, C. A., et al. "Source of Catalysis of Dephosphorylation of *p*-nitrophenyldiphenylphosphate by Metallonmicelles". *J. Chem. Soc., Perkin Trans.2*, 3: 419-425 (1996).

Scrimin, P., et al. "Metallonmicelles as Catalysts of the Hydrolysis of Carboxylic and Phosphate Acid Esters". *J. Org. Chem.*, 56: 161-166 (1991).

Balakrishnan, V.K., et al, "Catalytic Pathways in the Ethanolysis of Fenitrothion, an Organphosphorothioate Pesticide. A Dichotomy in the Behaviour of Crown/Cryptand Cation Complexing Agents". *Can. J. Chem.* 79: 151-173 (2001).

Bosch, E., et al., "Retention of Ionizable Compounds on HPLC, pH Scale in Methanol-Water and the pK and pH Values of Buffers". *Analytical Chemistry*. 68: 3651-3657 (1996).

Bosch, E., et al. "Hammett-Taft and Drago Models in the Prediction of Acidity Constant Values of Neutral and Cationic Acids in Methanol". *J. Chem. Soc., Perkin Trans.* 2: 1953-1958 (1999).

Brown, R.S., et al. "Hyrdrolysis of Neutral Phosphate and Phosphonate Esters Catalysed by $Co^{2+}$-chelates of Tris-inidazolyl Phosphines". *Inorganica Chimica Acta*. 108: 201-207 (1985).

Brown, R.S., et al. "Acyl and Phosphoryl Transfer to Methanol Promoted by Metal Ions". *J. Chem. Soc. Perkin Trans.* 2: 1039-1049 (2002).

Brown, R.S., et al. "$La^{3+}$-Catalyzed Methanolysis of Hydroxypropyl-p-nitrophenyl Phosphate as a Model for the RNA Transesterification Reaction". *39$^{th}$ IUPAC Congress and 86$^{th}$ Conference of the Canadian Society for Chemistry*. Ottawa, Ontario. Aug. 10-15 (2003) (Abstract).

Buncel, E., et al. "Alkali Metal Ion Catalysis in Nucleophilic Displacement by Ethoxide Ion on p-nitrophenyl Phenylphosphonate: Evidence for Multiple Metal Ion Catalysis". *Can. J. Chem.* 81: 53-63 (2003).

Clewly, R.G., et al. "Mono and Dinuclear $M^{2+}$ Chelates as Catalysts for the Hydrolysis of Organophosphate Triesters". *Inorganica Chimica Acta*. 157:233-238 (1989).

Desloges, W., et al. "$Zn^{2+}$-Catalyzed Methanolysis of Phosphate Triesters: A Process for Catalytic Degradation of the Organophosohorus Pesticides Paraoxon and Fenitrothion". *Inorganic Chemistry. submitted (2003)*.

Gans, P., et al. "Investigation of Equilibria in Solution. Determination of Equilibrium Constants with the HYPERQUAD Suite of Programs". *Talanta*. 43(10): 1739-1753 (1996).

Gibson, G., et al. "Potentiometric Titration of Metal Ions in Methanol". *Can. J. Chem.* 81: 495-504 (2003).

Ketelaar, J.A.A., et al. "Metal-catalysed Hydrolysis of Thiophosphoric Esters". *Nature*. 177: 392-393 (1956).

Khan, A., et al. "Strong $Zn^{2+}$ and $Co^{2+}$ Catalysis of the Methanolysis of Acetyl Imidazole and Acetyl Pyrazole". *Can. J. Chem.* 77: 1005-1008 (1999).

Nagelkerke, R., et al. "Alkali-metal Ion Catalysis and Inhibition in Nucleophilic Displacement Reactions at Carbon, Phosphorus and Sulfur Centres. IX. *p*-Nitrophenyl Diphenyl Phosphate". *Org. Biomol. Chem.* 1: 163-167 (2003).

Neverov, A.A., et al. "Catalysis of the Methanolysis of Acetylimidazole by Lanthanum Triflate". *Can. J. Chem.* 78: 1247-1250 (2000).

Neverov, A.A., et al. "$La^{3+}$-Catalyzed Methanolysis of Phosphate Diesters. Remarkable Rate Acceleration of the Methanolysis of Diphenyl Phosphate, Methyl *p*-Nitrophenyl Phosphate, and Bis(*p*-nitrophenyl) Phosphate". *Inorganic Chemistry*. 40: 3588-3595 (2001).

Neverov, A.A., et al. "Catalysis of Transesterification Reactions by Lanthanides —Unprecedented Acceleration of Methanolysis of Aryl and Alkyl Esters Promoted by $La(OTf)_3$ at Neutral $_s^s$pH and Ambient Temperatures". *Can. J. Chem.* 79: 1704-1710 (2001).

Neverov, A.A., et al. "Catalysis of the Methanolysis of Activated Amides by Divalent and Trivalent Metal Ions. The Effect of $Zn^{2+}$, $Co^{2+}$, and $La^{3+}$ on the Methanolysis of Acetylimidazole and Its $(NH^3)_5Co^{III}$ Complex". *J. Am. Chem. Soc.* 123: 210-217 (2001).

Neverov, A.A., et al. "Europium Ion Catalyzed Methanolysis of Esters at Neutral $_s^s$pH and Ambient Temperature. Catalytic Involvement of $Eu^{3+}(CH_3O\text{-})(CH_3OH)_x$". *Inorganic Chemistry*. 42:228-234 (2003).

Okano, T., et al. "Transesterification Catalyzed by Lanthanoid Tri-2-propoxides". *Chemistry Letters*. 246-258 (1995).

Rived, F., et al. "Dissociation Constants of Neutral and Charged Acids in Methyl Alcohol. The Acid Strength Resolution". *Analytica Chimica Acta.*, 374: 309-324 (1998).

Tsang, J.S.W., et al. $La^{3+}$-Catalyzed Methanolysis of Hydropropyl-*p*-nitrophenyl Phosphate as a Model for the RNA Transesterification Reaction. *J. Am. Chem. Soc.* 125: 1559-1566 (2003).

Tsang, J.S.W., et al. "Billion-fold Acceleration of the Methanolysis of Paraoxon Promoted by $La(OTf)_3$in Methanol". *J. Am. Chem. Soc.* 125: 7602-7607 (2003).

Yang, Y.-C., et al. "Decontamination of Chemical Warfare Agents". *Chem. Rev.* 92: 1729-1743 (1992).

Yang, Y.-C., et al. "Chemical Reactions for Neutralizing Chemical Warfare Agents". *Chemistry & Industry(London)*. 9: 334-337 (1995).

Yang, Y.-C., et al. "Peroxyhydrolysis of Nerve Agent VX and Model Compounds and Related Nucleophilic Reactions". *J. Chem. Soc., Perkin Trans.* 2: 607-613 (1997).

Yang, Y.-C. "Chemical Detoxification of Nerve Agent VX". *Acc. Chem. Res.* 32: 109-115 (1999).

* cited by examiner $\{Cu^{2+}[12]aneN_3(^-OCH_3)\}$

METHOD OF DECOMPOSING ORGANOPHOSPHORUS COMPOUNDS

RELATED APPLICATIONS

This application claims the benefit of the filing date of U.S. Provisional Patent Application No. 60/453,762, filed on Mar. 12, 2003, the contents of which are incorporated herein by reference in their entirety.

FIELD OF THE INVENTION

This invention relates to methods of decomposing organophosphorus compounds. The invention more particularly relates to metal ion and metal species catalysis of an alcoholysis reaction which converts toxic organophosphorus compounds into non-toxic compounds. The invention further relates to lanthanum ion catalyzed degradation of chemical warfare agents, insecticides and pesticides.

BACKGROUND OF THE INVENTION

The Chemical Weapons Convention was adopted by the Conference on Disarmament in Geneva on Sep. 3, 1992, entered into force on Apr. 29, 1997, and calls for a prohibition of the development, production, stockpiling and use of chemical weapons and for their destruction under universally applied international control. Eliminating the hazard of chemical warfare agents is desirable both in storage sites and on the battlefield. Decontamination of battlefields requires speed and ease of application of decontaminant. Surfaces involved pose a challenge for decontamination techniques since some surfaces absorb such agents, making decontamination difficult. Examples of surfaces that could be involved include those of tanks, ships, aircraft, weapons, electronic devices, ground, protective clothing and human skin. The decontaminants should not be corrosive, so that surfaces are not damaged during/following decontamination. An optimum solvent of a decontaminating method should provide ease of application, solubility of the chemical warfare agent, non-corrosiveness, and minimal environmental contamination. Since the establishment of the Convention, considerable effort has been directed toward methods of facilitating the controlled decomposition of organophosphorus compounds.

Aqueous decontamination systems, such as hydrolysis systems, have been used in the past, most notably for nerve agents, particularly for the G-agents tabun (GA), sarin (GB), soman (GD) and GF. However, hydrolysis reactions are not suitable for all chemical warfare nerve agents such as V-agents VX (S-2-(diisopropylamino)ethyl O-ethyl methylphosphonothiolate) and Russian-VX (S-2-(diethylamino) ethyl O-isobutyl methylphosphonothiolate), whose decontamination chemistries are very similar to one another (Yang, 1999). The V-agents are about 1000-fold less reactive with hydroxide than the G-agents (due to their poor solubility in water under basic conditions), and they produce product mixtures containing the hydrolytically stable, but toxic, thioic acid byproduct.

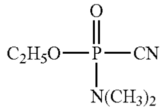

Tabun (GA)

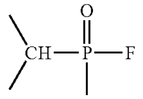

Sarin (GB)

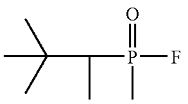

Soman (GD)

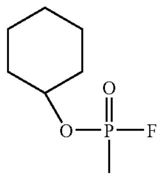

GF

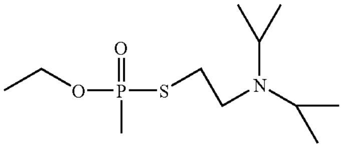

VX

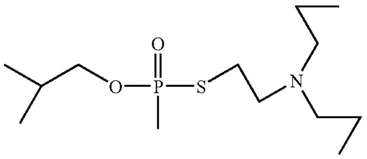

Russian-VX

Although some chemical warfare agents are water soluble, they may be applied in combination with a polymer so that, being thickened, they adhere well to surfaces. These “thickened” agents are only minimally soluble in water. In the case of decomposition using a hydrolysis reaction, products in which a phosphorus-sulfur bond is preserved are common; these are toxic in their own right and are relatively resistant to further reaction. Another disadvantage of an aqueous decontamination system is that hydrolysis reactions are not catalytic, and therefore require stoichiometric amounts of reagents. Furthermore, commonly used aqueous methods, due to their alkaline pH, are not suitable for decontamination of human skin. Yet another disadvantage of aqueous decontamination methods is the caustic wastewater produced as an end product, which poses a challenge for disposal.

Historically, decontamination of chemical warfare agents has been effected using hydrolysis or oxidation using bleach or alkali salts. Bleach is corrosive to skin, rubber, and metal surfaces and is ineffective in cold weather conditions. Alkali salts require excess hydroxide ion in order for the reaction to go to completion rapidly, thus resulting in a caustic product. Non-catalytic methanolysis of V-agents has been studied, wherein the reaction of VX with alkoxide leads primarily to a displacement of the $SR^-$ group (Yang et al., 1997).

Transition metal ions and lanthanide series ions and certain mono- and dinuclear complexes thereof are known to promote hydrolysis of neutral phosphate and/or phosphonate esters. However, the available literature on the hydrolysis of phosphothiolate (P═S) esters and phosphothiolates is quite sparse with only the softer ions such as $Cu^{2+}$, $Hg^{2+}$ and $Pd^{2+}$ showing significant catalysis. The lack of examples may be due to reduced activity of P═S esters, their poor aqueous solubility and the fact that anionic hydrolytic products bind to the metal ions thereby inhibiting further catalysis.

There is a need for a viable catalytic decontamination method which is inexpensive, has high catalyst turnover, and occurs at relatively neutral pH and ambient temperature, and most importantly, proceeds rapidly, e.g. $t_{1/2}<1$ min.

BRIEF STATEMENT OF THE INVENTION

According to one aspect of the invention there is provided a method for decomposing an organophosphorus compound comprising subjecting said organophosphorus compound to an alcoholysis reaction in a medium comprising non-radioactive metal ions and at least a trace amount of alkoxide ions, wherein, through said alcoholysis reaction, said organophosphorus compound is decomposed.

In one embodiment of the invention, said organophosphorus compound has the following formula (10):

(10)

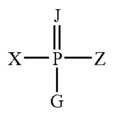

where:

J is O or S;

X, G, Z are the same or different and are selected from the group consisting of Q, OQ, QA, OA, F, Cl, Br, I, QS, SQ and C≡N;

Q is hydrogen or a substituted or unsubstituted branched, straight-chain or cyclic alkyl group having 1–100 carbon atoms; and A is a substituted or unsubstituted aryl group selected from the group consisting of phenyl, biphenyl, benzyl, pyridyl, naphthyl, polynuclear aromatic, and aromatic and non-aromatic heterocyclic;

wherein, when X, G, Z are the same, (i) X, G, Z are not Q; or (ii) Q is not H; and wherein said substituents are selected from the group consisting of Cl, Br, I, F, nitro, nitroso, Q, alkenyl, OQ, carboxyalkyl, acyl, $SO_3H$, $SO_3Q$, S═O(Q), $S(═O)_2Q$, amino, alkylamino (NHQ), arylamino (NHA), alkylarylamino, dialkylamino and diarylamino.

In some embodiments, said medium is a solution further comprising a solvent selected from the group consisting of methanol, substituted and unsubstituted primary, secondary and tertiary alcohols, alkoxyalkanol, aminoalkanol, and combinations thereof.

In a preferred embodiment, said organophosphorus compound has at least one phosphorus atom double bonded to an oxygen or a sulfur atom.

In another embodiment, said medium further comprises a non-inhibitory buffering agent.

In yet another embodiment said buffering agent is selected from the group consisting of anilines, N-alkylanilines, N,N-dialkylanilines, N-alkylmorpholines, N-alkylimidazoles, 2,6-dialkylpyridines, primary, secondary and tertiary amines, trialkylamines, and combinations thereof.

In another embodiment, said medium is a solution further comprising a solvent selected from the group consisting of methanol, ethanol, n-propanol, iso-propanol, n-butanol, 2-butanol, methoxyethanol, and combinations thereof.

In further embodiments, said solution further comprises a solvent selected from the group consisting of nitriles, esters, ketones, amines, ethers, hydrocarbons, substituted hydrocarbons, unsubstituted hydrocarbons, chlorinated hydrocarbons, and combinations thereof.

In further embodiments, said medium further comprises alkoxide ions in addition to said at least a trace amount of alkoxide ions.

In further embodiments, the concentration of said alkoxide ions is about 0.1 to about 2 equivalents of the concentration of the metal ions.

In further embodiments, the concentration of said alkoxide ions is about 1 to about 1.5 equivalents of the concentration of the metal ions.

In further embodiments, said medium is prepared by combining a metal salt and an alkoxide salt with at least one of alcohol, alkoxyalkanol and aminoalkanol.

In further embodiments, said metal ions are selected from the group consisting of lanthanide series metal ions, transition metal ions, and combinations thereof.

In further embodiments, said metal ions are selected from the group consisting of lanthanide series metal ions, copper, platinum, palladium, zinc, nickel, yttrium, scandium ions, and combinations thereof.

In further embodiments, said metal ions are selected from the group consisting of $Cu^{2+}$, $Pt^{2+}$, $Pd^{2+}$, $Zn^{2+}$, $Y^{3+}$, $Sc^{3+}$, $Ce^{3+}$, $La^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and combinations thereof.

In further embodiments, said metal ions are lanthanide series metal ions.

In further embodiments, said lanthanide series metal ions are selected from the group consisting of $Ce^{3+}$, $La^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and combinations thereof.

In further embodiments, said metal ions are selected from the group consisting of $Cu^{2+}$, $Pt^{2+}$, $Pd^{2+}$, $Zn^{2+}$, and combinations thereof.

In further embodiments, said metal ions are selected from the group consisting of $Y^{3+}$, $Sc^{3+}$, and combinations thereof.

In further embodiments, said metal ion is $La^{3+}$.

In further embodiments, said organophosphorus compound is a pesticide.

In further embodiments, said organophosphorus compound is an insecticide.

In further embodiments,said organophosphorus compound is paraoxon.

In further embodiments, said organophosphorus compound is a chemical warfare agent.

In further embodiments, said organophosphorus compound is a G-agent.

In further embodiments, said organophosphorus compound is selected from the group consisting of VX and Russian-VX.

In further embodiments, said organophosphorus compound is a nerve agent.

In further embodiments, said chemical warfare agent is combined with a polymer.

In further embodiments, said medium further comprises one or more ligands.

In further embodiments, said ligand is selected from the group consisting of 2,2'-bipyridyl, 1,10-phenanthryl, 2,9-dimethylphenanthryl, crown ether, and 1,5,9-triazacyclododecyl.

In further embodiments, said ligand further comprises solid support material.

In further embodiments, said solid support material is selected from a polymer, silicate, aluminate, and combinations thereof.

In further embodiments, said medium is a solid.

In further embodiments, said medium is a solution.

In further embodiments, said solution is disposed on an applicator.

In further embodiments, the concentration of said alkoxide ions is about 0.5 to about 1.5 equivalents of the concentration of the metal ions.

In another broad aspect, the invention provides a kit for decomposing an organophosphorus compound comprising a substantially non-aqueous medium for an alcoholysis reaction, said medium comprising non-radioactive metal ions and at least a trace amount of alkoxide ions.

In a first embodiment, said medium is contained in an ampule.

In a second embodiment, the kit comprises an applicator bearing the medium, said applicator being adapted so that the medium is applied to the organophosphorus compound and the compound decomposes.

In some embodiments, the kit further comprises written instructions for use.

BRIEF DESCRIPTION OF THE DRAWINGS

For a better understanding of the invention and to show more clearly how it may be carried into effect, reference will now be made by way of example to the accompanying drawings, which illustrate aspects and features according to preferred embodiments of the present invention, and in which.

○, ${}_s^s$pH 8.23; and

●, ${}_s^s$pH 7.72.

Figure 3:
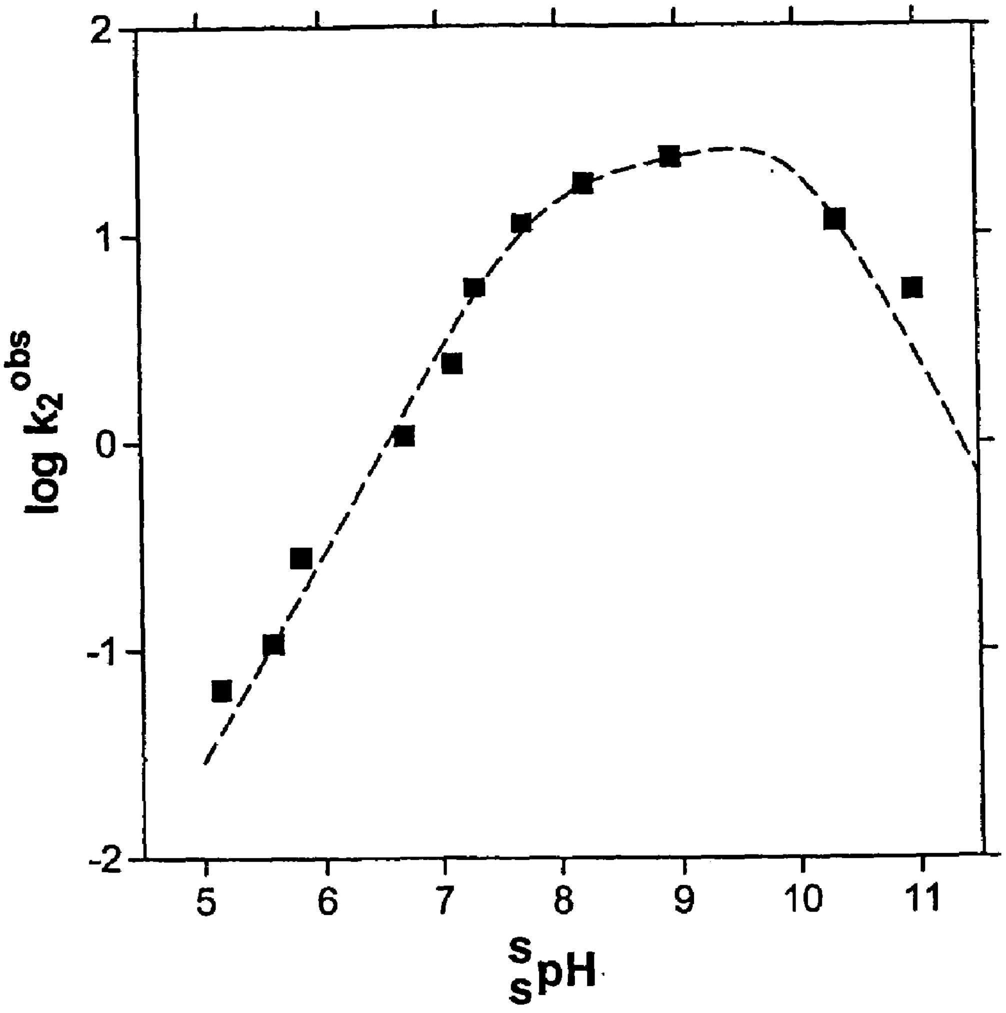

FIG. 3 shows a plot of the log $k_2^{obs}$ ($M^{-1}s^{-1}$) vs. ${}_s^s$pH for $La^{3+}$-catalyzed methanolysis of paraoxon at 25° C. The dotted line through the data was computed on the basis of a fit of the $k_{obs}$ data to equation 3, the two dominant forms being $La_2(OCH_3)_2$ and $La_2(OCH_3)_3$.

Figure 4:
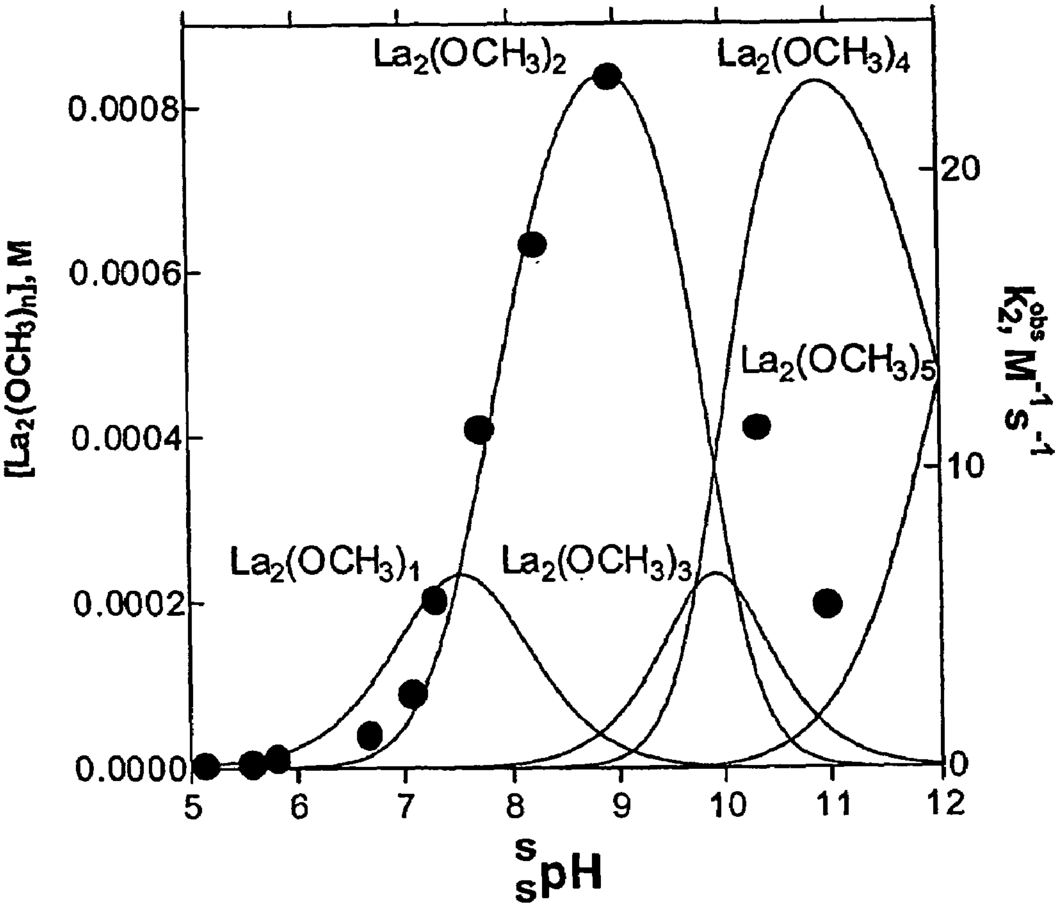

FIG. 4 shows a speciation diagram for the distribution of $La_2(OCH_3)_n$ forms in methanol, n=1–5, as a function of ${}_s^s$pH, calculated for $[La(OTf)_3]=2\times10^{-3}$ M. Data represented as (●) correspond to second order rate constants ($k_2^{obs}$) for $La^{3+}$-catalyzed methanolysis of paraoxon presented in Table 13.

Figure 5:
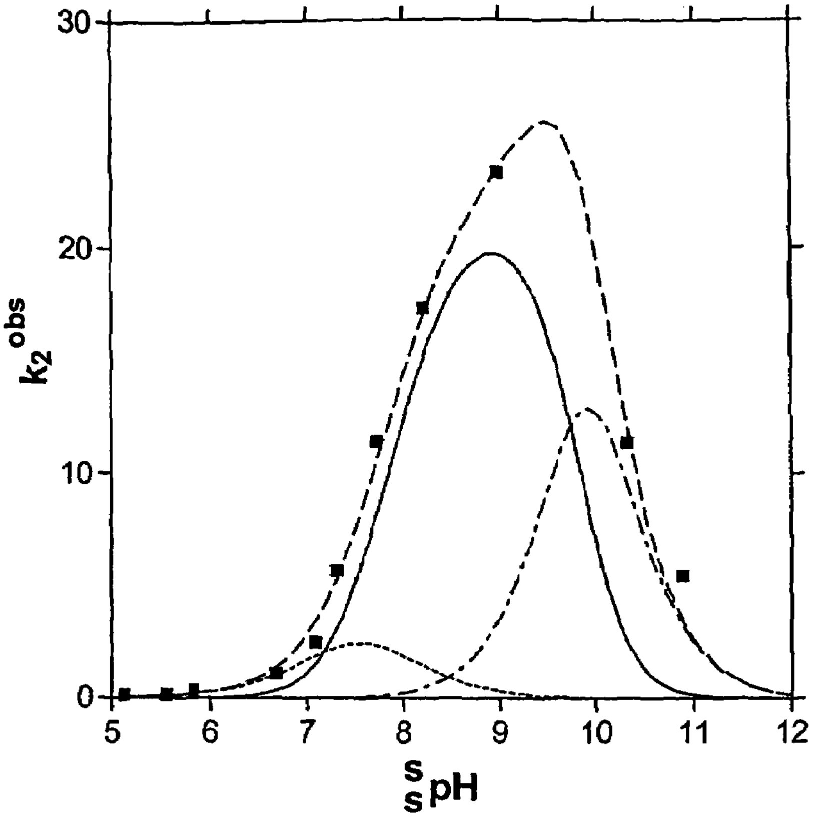

FIG. 5 shows a plot of the predicted $k_2^{obs}$vs. ${}_s^s$pH rate profile for $La^{3+}$-catalyzed methanolysis of paraoxon (--------) based on the kinetic contributions of $La_2(OCH_3)_1$, (......); $La_2(OCH_3)_2$ (solid line) and $La_2(OCH_3)_3$, (._._._) computed from the $k_2^{2:1}$, $k_2^{2:2}$ and $k_2^{2:3}$ rate constants (Table 14), and their speciation (FIG. 4); data points (■) are experimental $k_2^{obs}$ rate constants from Table 13.

Figure 6:
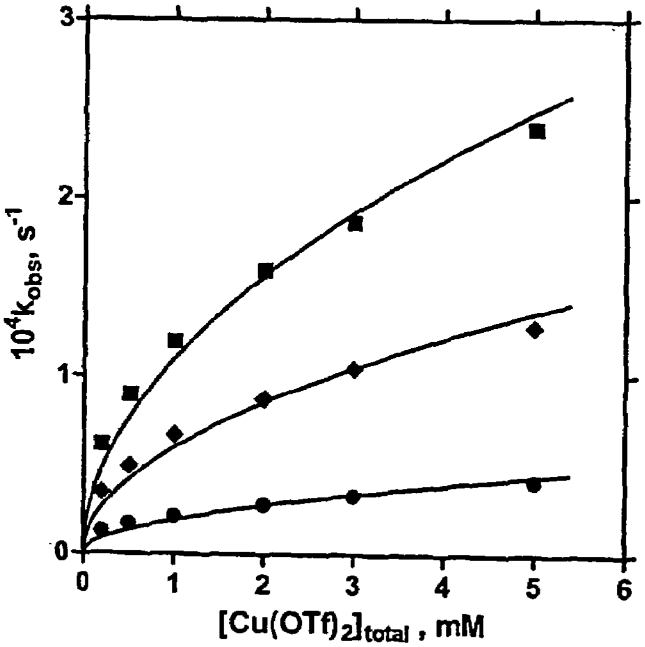

FIG. 6 shows the effect of copper triflate (in the presence of equimolar ligand and 0.5 equivalents of methoxide) on the rate of methanolysis of fenitrothion as a plot of the $k_{obs}$ vs. total concentration of $Cu(OTf)_2$ for the methanolysis of fenitrothion catalyzed by various species at T=25° C. and $[OCH_3]/[Cu^{2+}]_t=0.5$, when ligand is used, $[Cu^{2+}]_t$=[Ligand], where ●, {$Cu^{2+}$:no ligand:($^-OCH_3$)};

♦, {$Cu^{2+}$:phen:($^-OCH_3$)}; and

■, {$Cu^{2+}$:bpy:($^-OCH_3$)}.

Figure 7:
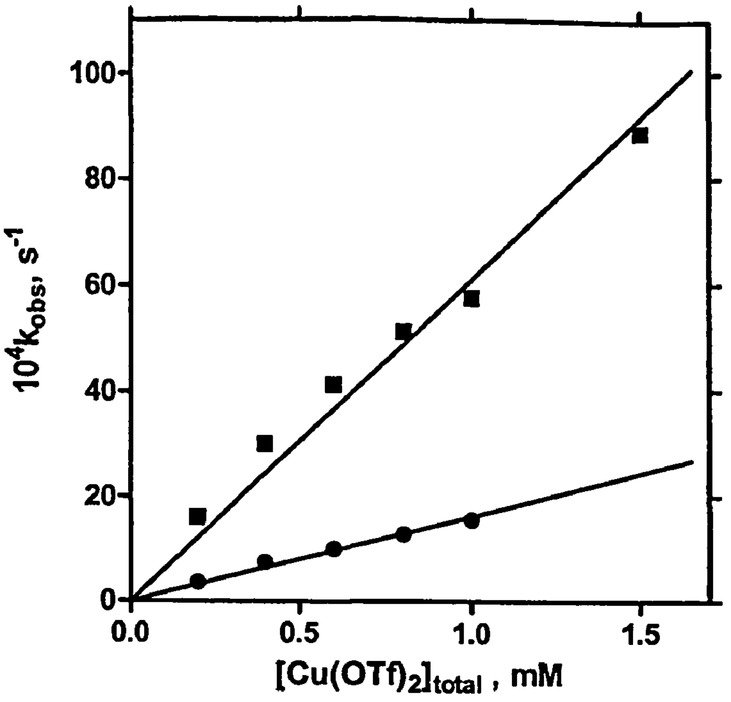

FIG. 7 shows the effect of $Cu^{2+}$:[12]ane$N_3$:($^-OCH_3$) (copper triflate in the presence of equimolar ligand and 0.5 equivalents of methoxide) on the rate of methanolysis of paraoxon (●) and fenitrothion (■) as a plot of the $k_{obs}$ vs. total concentration of $Cu(OTf)_2$ conducted at T=25° C.

Figure 8:
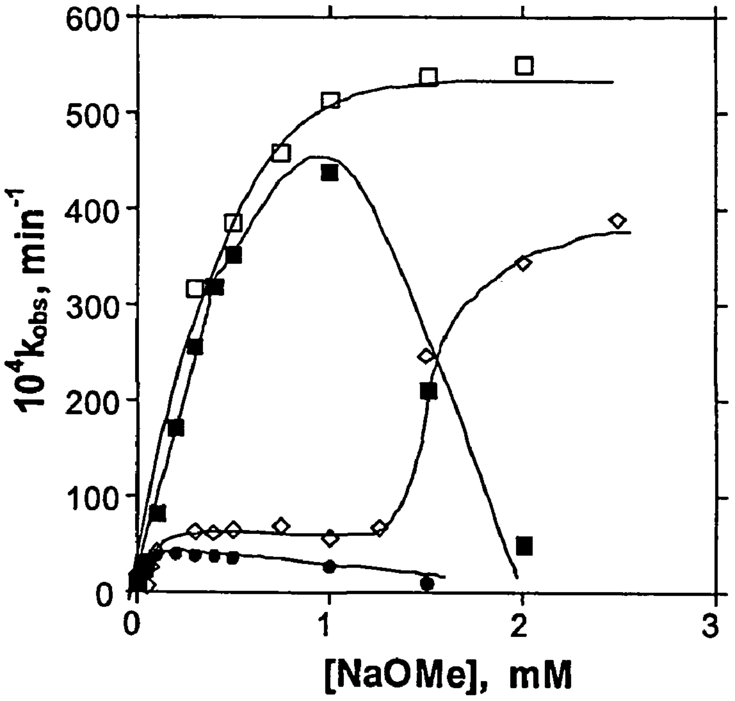

FIG. 8 shows the effect of methoxide ion concentration on the rate of $Zn^{2+}$-catalyzed methanolysis of paraoxon as plots of $k_{obs}$ vs added $NaOCH_3$ for the methanolysis of paraoxon in the presence of 1 mM $Zn(ClO_4)$, where:

●, no added ligand;

♦1 mM phen;

■, 1 mM diMephen; and

□, 1 mM [12]ane$N_3$ (lines through the data drawn as visual aid only).

Figure 9A:
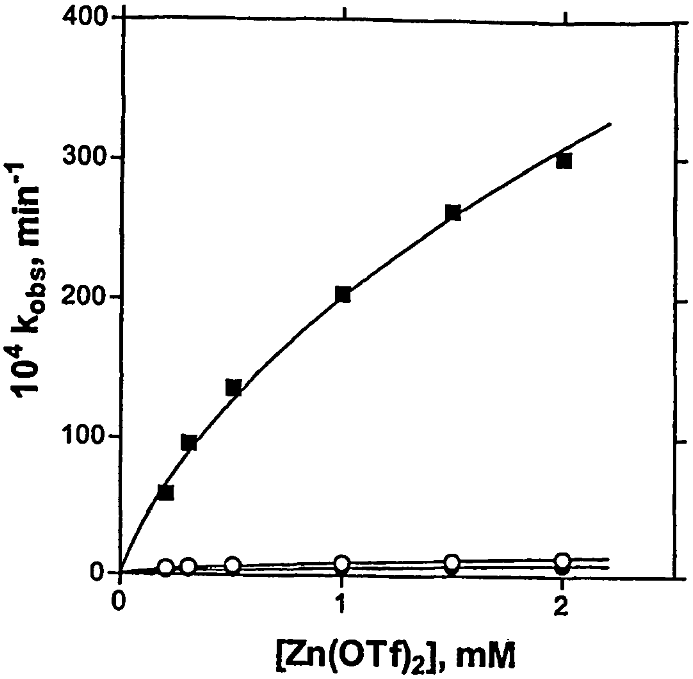

FIG. 9A shows the catalyzed methanolysis of fenitrothion as a plot of $k_{obs}$ vs. concentration of zinc ion ($Zn(OTf)_2$) alone, and in the presence of equimolar ligand at constant $[(-OCH_3)]/[Zn^{2+}]_{total}$ ratios, where:

●, no ligand, $[(^-OCH3)]/[Zn^{2+}]_{total}$=0.3;

○, phen, $[(^-OCH_3)]/[Zn^{2+}]_{total}$=0.5; and

■, diMephen, $[(^-OCH_3)]/[Zn^{2+}]_{total}$=1.0

Figure 9B:
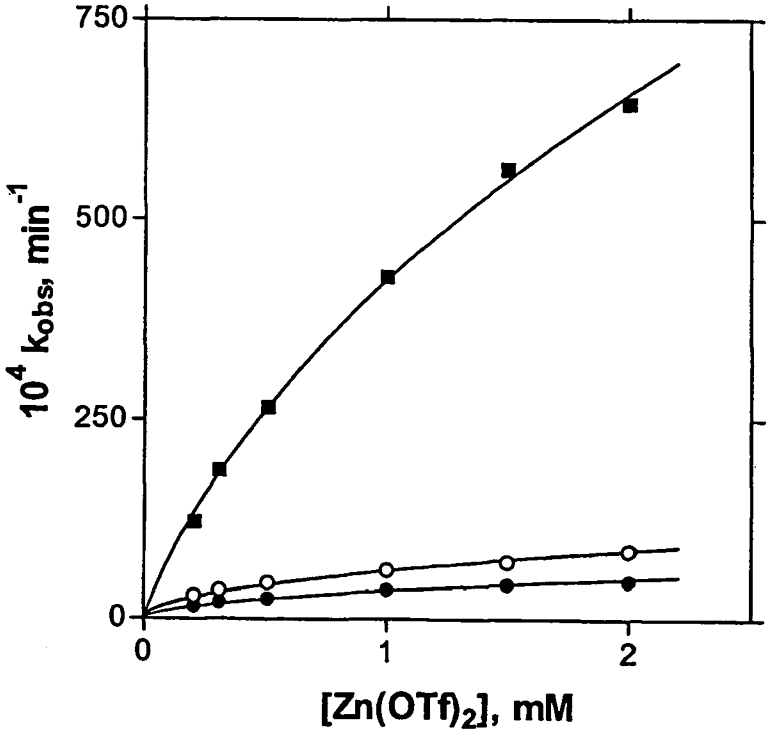

FIG. 9B shows the catalyzed methanolysis of paraoxon as a plot of $k_{obs}$ vs. concentration of zinc ion ($Zn(OTf)_2$) alone and in the presence of equimolar ligand at constant $[(^-OCH_3)]/[Zn^{2+}]_{total}$ratios, where:

●, no ligand, $[(^-OCH_3)]/[Zn^{2+}]_{total}$=0.3;

○, phen, $[(^-OCH_3)]/[Zn^{2+}]_{total}$=0.5; and

■, diMephen, $[(^-OCH_3)]/[Zn^{2+}]_{total}$=1.0.

Figure 10:
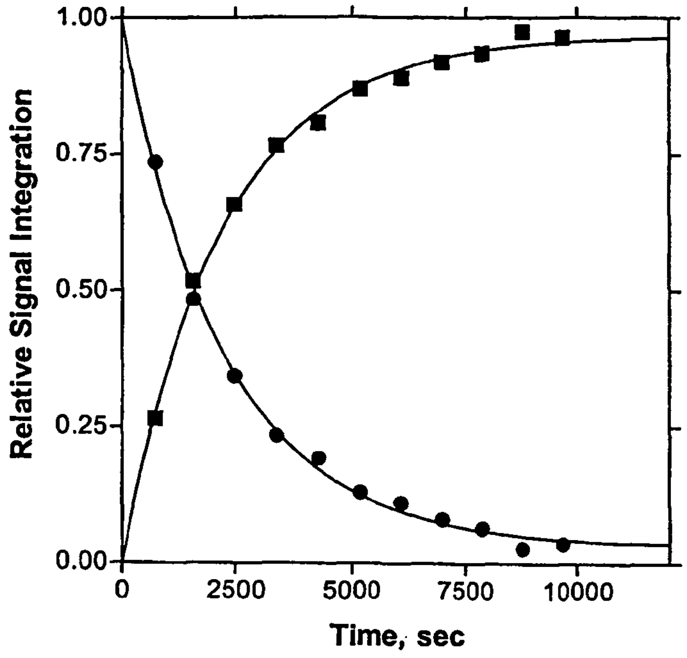

FIG. 10 shows the disappearance of paraoxon (●) and appearance of diethyl methyl phosphate (■) product over time for a methanolysis reaction in the presence of zinc ion, methoxide, and ligand in deuterated methanol in a plot of relative signal integration of the reagent and product $^{31}P$ NMR signals for a system containing 15 mM paraoxon, 1 mM $Zn(OTf)_2$, 1 mM $NaOCH_3$ and 1 mM diMephen at T=25° C.

Figure 11:
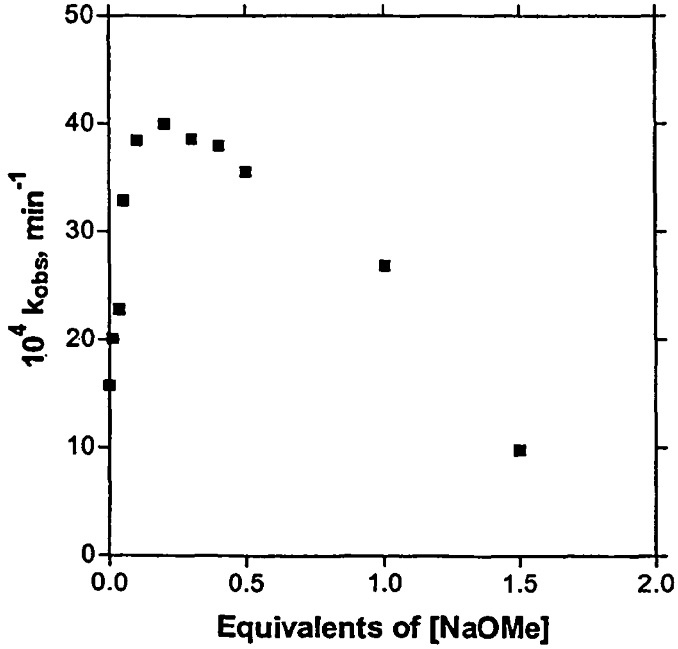

FIG. 11 shows the effect of increasing concentration of methoxide on the rate of $Zn^{2+}$-catalyzed methanolysis of paraoxon in a plot of the pseudo-first order rate constants ($k_{obs}$) for methanolysis of paraoxon in the presence of 1 mM $Zn(OTf)_2$ and absence of added ligand as a function of added $NaOCH_3$.

Figure 12:
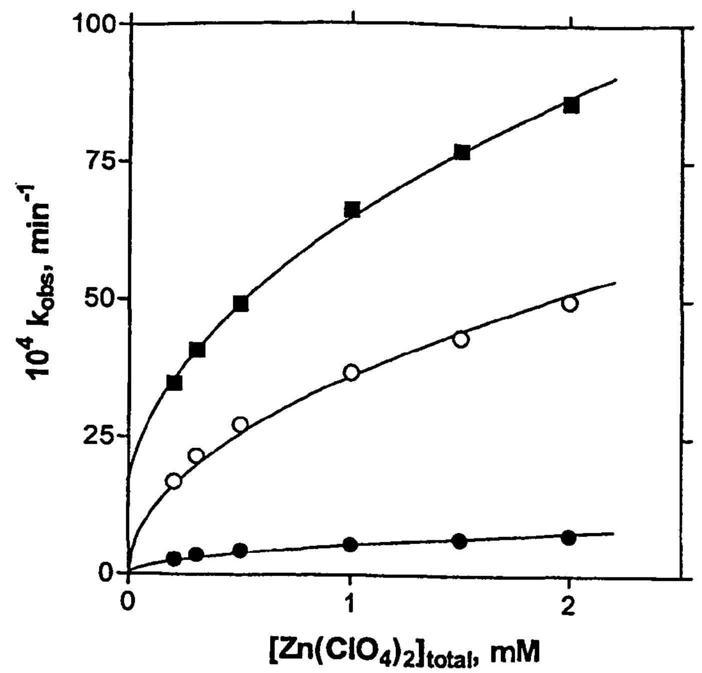

FIG. 12 shows the effect of zinc ion concentration on the rate of $Zn^{2+}$-catalyzed methanolysis of paraoxon as plots of the $k_{obs}$ for the methanolysis of fenitrothion (●), paraoxon (○) and p-nitrophenyl acetate (■) vs. $[Zn(ClO_4)_2]$ at a constant $[Zn^{2+}(^-OCH_3)]/[Zn^{2+}]_{total}$ ratio of 0.3, T=25° C. Lines through the data are calculated on the basis of fits to equation (6).

Figure 13A:
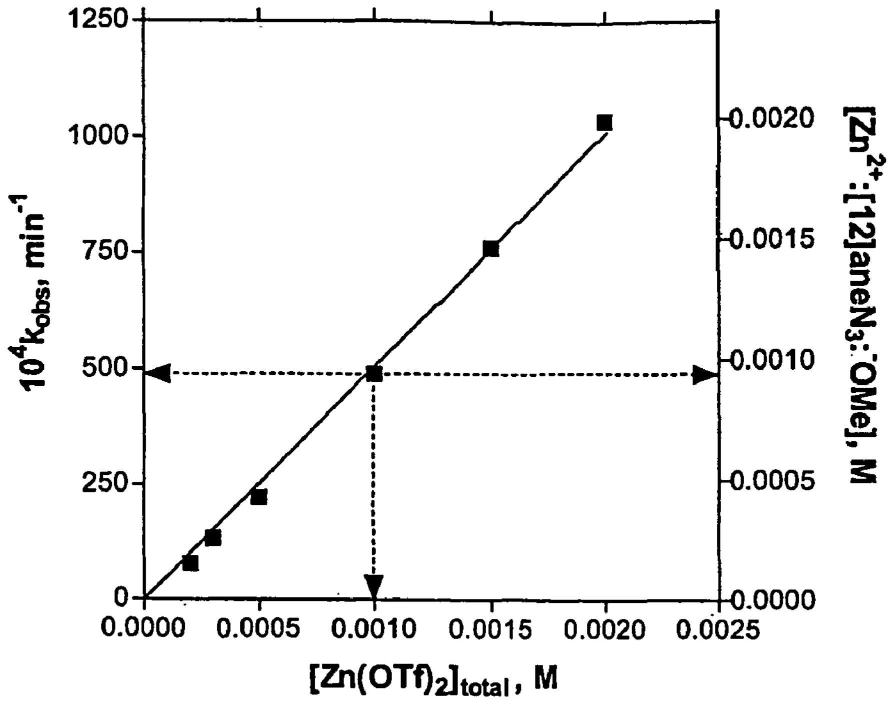

FIG. 13A shows the effect of $Zn^{2+}$:[12]ane$N_3$ on the rate of $Zn^{2+}$-catalyzed methanolysis of paraoxon as a plot of $k_{obs}$ for methanolysis of paraoxon as a function of $[Zn(OTf)_2]_{total}$ containing equimolar [12]ane$N_3$ and $NaOCH_3$, T=25° C. Right axis gives [$Zn^{2+}$:[12]ane$N_3$:($^-OCH_3$)] determined by Hyperquad™ fitting of titration data. The arrows are presented as a visual aid to connect the various species concentrations with the kinetic rate constant.

Figure 13B:
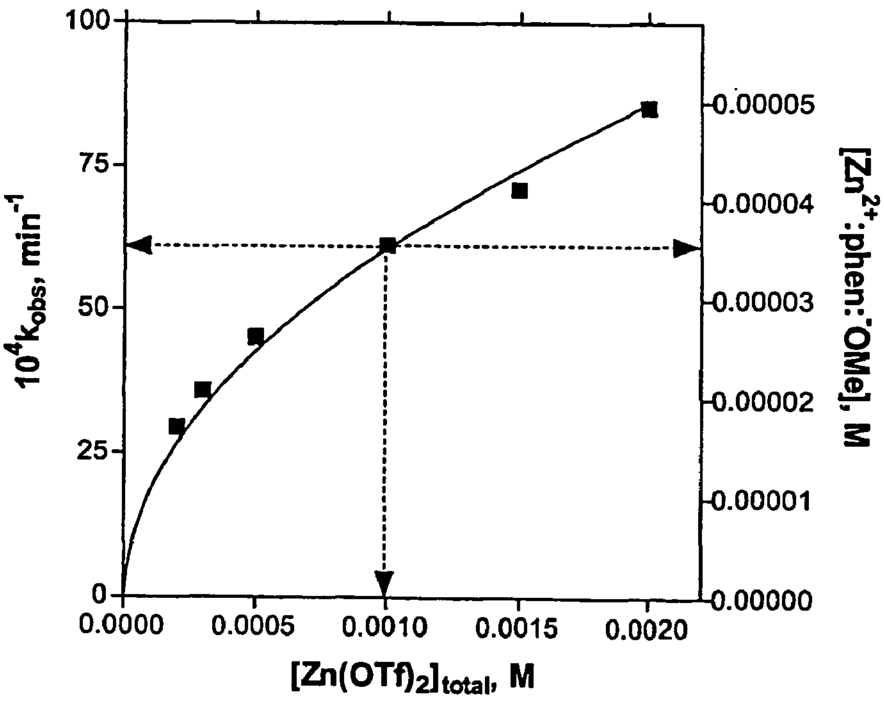

FIG. 13B shows the effect of $Zn^{2+}$:phen on the rate of $Zn^{2+}$-catalyzed methanolysis of paraoxon as a plot of $k_{obs}$ for methanolysis of paraoxon as a function of $[Zn(OTf)_2]_{total}$ containing equimolar phen and $NaOCH_3$, T=25° C. Right axis gives $[Zn^{2+}$:phen:$(^-OCH_3)]$ determined by Hyperquad™ fitting of titration data. The arrows are presented as a visual aid to connect the various species concentrations with the kinetic rate constant.

Figure 14:
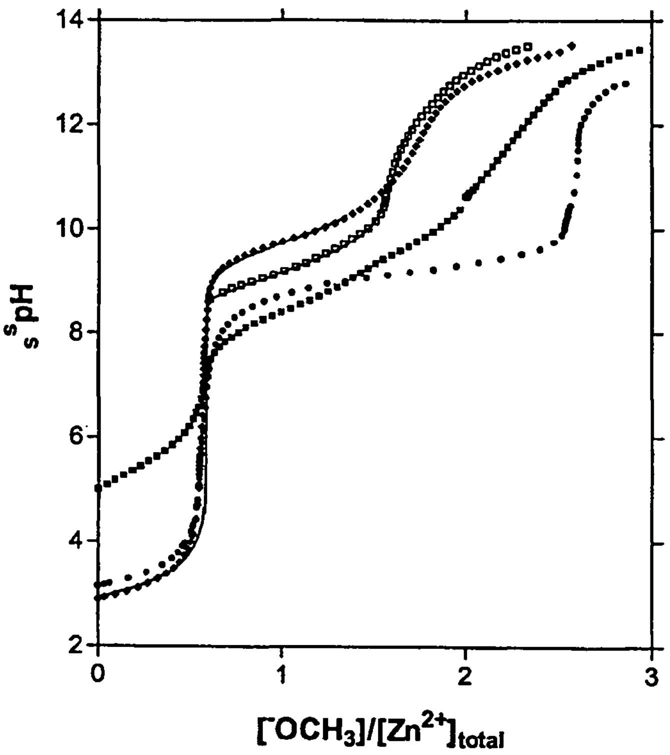

FIG. 14 shows the titration profiles obtained by potentiometric titration of 2 mM $Zn(OTf)_2$ with no added ligand (●), with 2 mM phen (♦), with 2 mM diMephen (■), with 2 mM [12]ane$N_3$ (□) and with 1.2 mM added $HClO_4$. Lines through the titration curves with phen and [12]ane$N_3$ were derived from Hyperquad™ fitting of the data.

DETAILED DESCRIPTION OF THE INVENTION

According to a broad aspect of the invention there is provided a method of decomposing an organophosphorus compound by combining the organophosphorus compound with a substantially non-aqueous medium comprising alcohol, alkoxyalkanol or aminoalkanol, metal ions and at least a trace amount of alkoxide ions. When so combined the organophosphorus compound undergoes an alcoholysis reaction and forms a less toxic or non-toxic compound.

More particularly, the invention provides a method of increasing the rate of decomposition of an organophosphorus compound by combining the compound with a catalytic species formed in a substantially non-aqueous medium comprising metal ions; alcohol, alkoxyalkanol or aminoalkanol; and alkoxide ions. In some embodiments, the medium is a solution.

As used herein, the term "alcohol" means a compound which comprises an R—OH group, for example, methanol, primary alcohols, and substituted or unsubstituted secondary alcohols, tertiary alcohols, alkoxyalkanol, aminoalkanol, or a mixture thereof.

As used herein, "substantially non-aqueous medium" means an organic solvent, solution, mixture or polymer. As it is very difficult to obtain anhydrous alcohol, a person of ordinary skill in the art would recognize that trace amounts of water may be present. For example, absolute ethanol is much less common than 95% ethanol. However, the amount of alcohol present in a medium or solution according to the invention should not have so much water present as to inhibit the alcoholysis reaction, nor should a substantial amount of hydrolysis occur.

As used herein, the term "organophosphorus compound" includes compounds which comprise a phosphorus atom doubly bonded to an oxygen or a sulfur atom. In preferred embodiments such organophosphorus compounds are deleterious to biological systems, for example, a compound may be an acetylcholine esterase inhibitor, a pesticide or a chemical warfare agent.

As used herein, the term "decomposing an organophosphorus compound" refers to rendering a deleterious organophosphorus compound into a less toxic or non-toxic form.

Decomposition of an organophosphorus compound according to the invention may be carried out in solution form, or in solid form. Examples of such decomposition include, applying catalyst as a solution directly to a solid chemical warfare agent or pesticide. Such a solution would be for example, an appropriately buffered alcoholic, alkoxyalkanolic or aminoalkanolic solution comprising metal ions and alkoxide ions, in which one or more catalytic species forms spontaneously, which may be applied to a surface which has been contacted with an organophosphorus agent.

As used herein, the term "catalytic species" means a molecule or molecules, comprising metal ions and alkoxide ions, whose presence in an alcoholic, alkoxyalkanolic or aminoalkanolic solvent containing an organophosphorus compound increases the rate of alcoholysis of the organophosphorus compound relative to its rate of alcoholysis in the solvent without the catalytic species.

As used herein, the term "appropriately buffered" means that the ${}_s^s$pH of a solution is controlled by adding non-inhibitory buffering agents, or by adding about 0.1 to about 2.0 equivalents of alkoxide ion per equivalent of metal ion.

As used herein, the term "${}_s^s$pH" is used to indicate pH in a non-aqueous solution (Bosch et al., 1999, Rived et al., 1998, Bosch et al., 1996). One skilled in the art will recognize that if a measuring electrode is calibrated with aqueous buffers and used to measure pH of an aqueous solution, the term ${}_w^w$pH is used. If the electrode is calibrated in water and the 'pH' of a neat methanol solution is then measured, the term ${}_s^w$pH is used, and if the latter reading is made, and a correction factor of 2.24 (in the case of methanol) is added, then the term ${}_s^s$pH is used.

As used herein, the term "non-inhibitory agent or compound" means that the agent or compound does not substantially diminish the rate of a catalyzed reaction when compared to the rate of the reaction in the absence thereof.

As used herein, the term "inhibitory agent or compound" means that the agent or compound does substantially diminish the rate of a catalyzed reaction when compared to the rate of the reaction in the absence thereof.

As used herein, the term "metal species" means a metal in an oxidation state of zero to 9.

As used herein, the term "mononuclear" or "monomeric" means a species comprising one metal atom.

In an embodiment of the invention, the catalytic species is a metal alkoxide species of the stoichiometry $\{M^{n+}(^-OR)_m\ L_g\}_s$ where M is a metal selected from lanthanide series metals or transition metals; n is the charge on the metal which may be 1 to 9, most preferably 2 to 4; $^-OR$ is alkoxide; m is the number of associated alkoxide ions and may be 1, 2, . . . , n−1, n, n+1, n+2, . . . n+6, most preferably 1 to n−1; s is 1 to 100; L is ligand; g is the number of ligands complexed to the metal ion, and may be 0 to 9; where g is greater than 1, the ligands may be the same or different. Examples of this embodiment include the lanthanum dimer $\{La^{3+}(^-OMe)\}_2$ and copper monomer $\{Cu^{2+}(^-OMe)L\}$.

The inventors contemplate an embodiment wherein the oxidation state of the metal atom is zero. For example, it is well known in the art that transition metals having an oxidation state of zero may be reactive and may form complexes. Copper is an example of such a metal, and it is expected that $Cu^0$ may catalyze alcoholysis of organophosphorus compounds according to the invention.

As used herein, the term "ligand" means a species containing a donor atom or atoms that has a non-bonding lone pair or pairs of electrons which are donated to a metal centre to form one or more metal-ligand coordination bonds. In this way, ligands bond to coordination sites on a metal and thereby limit dimerization and prevent further oligomerization of the metal species, thus allowing a greater number of active mononuclear species to be present than is the case in the absence of ligand or ligands.

As used herein, the term "$\{M^{n+}$:L:$^-OR\}$" (which differs from the above described system, $\{M^{n+}(^-OR)_mL_g\})_s$ by the use of the symbol ":" between constituents of the brace "{}") is used when no stoichiometry is defined for a system comprising metal ions ($M^{n+}$), ligand (L), and alkoxide ($^{-}OR$). This technique is meant to encompass any and all catalytically active stoichiometries thereof including but not limited to dimers, trimers and longer oligomers, monoalkoxides, dialkoxides, polyalkoxides, etc.

In another embodiment of the invention, the catalytic species has the general formula 20:

(20)

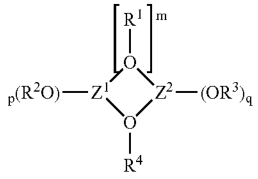

where $Z^1$ and $Z^2$ are the same or different non-radioactive lanthanide, copper, platinum or palladium ions;

$R^1$, $R^2$, $R^3$ and $R^4$ are each independently alkyl groups selected from a branched, cyclic or straight-chain hydrocarbon containing 1–12 carbon atoms, preferably 1–4 carbon atoms;

p is a number from 1–6; and m and q are each independently zero or 1 or more, preferably 1–5, such that the dimer has a net charge of zero.

In another embodiment of the invention, the catalytic species has the general formula 20:

where $Z^1$ and $Z^2$ are the same or different non-radioactive lanthanide series metal ions, copper, platinum or palladium ions;

$R^1$, $R^2$, $R^3$ and $R^4$ are each independently alkyl groups selected from a branched, cyclic or straight-chain hydrocarbon containing 1–12 carbon atoms, preferably 1–4 carbon atoms;

p is a number from 1–6; and m and q are each independently zero or 1 or more, preferably 1–5, such that the dimer has a net charge of zero.

In another embodiment of the invention, the catalytic species has the general formula 20:

where $Z^1$ and $Z^2$ are the same or different non-radioactive lanthanide series metal ions, and/or transition metal ions;

$R^1$, $R^2$, $R^3$ and $R^4$ are each independently alkyl groups selected from a branched, cyclic or straight-chain hydrocarbon containing 1–12 carbon atoms, preferably 1–4 carbon atoms;

p is a number from 0–6; and m and q are each independently zero or 1 or more, preferably 1–5, such that the dimer has a net positive charge.

In another embodiment of the invention, the catalytic species has the general formula 20:

where $Z^1$ and $Z^2$ are the same or different non-radioactive lanthanide series metal ions, and/or transition metal ions;

$R^1$, $R^2$, $R^3$ and $R^4$ are each independently alkyl groups selected from a branched, cyclic or straight-chain hydrocarbon containing 1–12 carbon atoms, preferably 1–4 carbon atoms;

p is a number from 1–6; and m and q are each independently zero or 1 or more, preferably 1–5, such that the dimer has a net positive charge.

In another embodiment of the invention, the catalytic species has the general formula 30:

$${}_a(R^2O)\text{-}Z^1\text{-}(OR^3)_b \qquad (30)$$

where $Z^1$ is a non-radioactive lanthanide, copper, platinum or palladium ion;

$R^2$ and $R^3$ are each independently alkyl groups selected from a branched, cyclic or straight-chain hydrocarbon containing 1–12 carbon atoms, preferably 1–4 carbon atoms;

a is a number from 1–3; and b is zero or 1 or more, such that the catalytic species has a net charge of zero.

In another embodiment of the invention, the catalytic species has the general formula 30:

where $Z^1$ is a non-radioactive lanthanide series metal ion or a transition metal ion;

$R^2$ and $R^3$ are each independently alkyl groups selected from a branched, cyclic or straight-chain hydrocarbon containing 1–12 carbon atoms, preferably 1–4 carbon atoms;

a is a number from 1–3; and b is zero or 1 or more, such that the catalytic species has a net positive charge.

Another embodiment of the invention, the catalytic species has the general formula 30:

where $Z^1$ is a non-radioactive lanthanide series metal ion or a transition metal ion;

$R^2$ and $R^3$ are each independently alkyl groups selected from a branched, cyclic or straight-chain hydrocarbon containing 1–12 carbon atoms, preferably 1–4 carbon atoms;

a is a number from 1–3; and b is zero or 1 or more, such that the catalytic species has a net positive charge;

wherein unoccupied coordination sites on the metal may be occupied by one or more ligands.

In another embodiment of the invention, the catalytic species has the general formula 40:

(40)

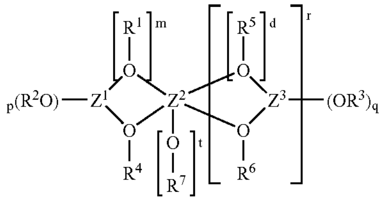

where $Z^1$, $Z^2$ and $Z^3$ are the same or different non-radioactive lanthanide, copper, platinum or palladium ions;

$R^1$, $R^2$, $R^3$, $R^4$, $R^5$, $R^6$ and $R^7$ are each independently alkyl groups selected from a branched, cyclic or straight-chain hydrocarbon containing 1–12 carbon atoms, preferably 1–4 carbon atoms;

p is a number from 1–4;

m, d, q and t are each independently zero or 1 or more, preferably 1–5, such that the oligomer has a net charge of zero; and r is a number from 0 to 100, or in the case of polymeric material may be greater than 100.

In yet another embodiment of the invention, the catalytic species has the general formula 40:

where $Z^1$, $Z^2$ and $Z^3$ are the same or different non-radioactive lanthanide series metal ions, or transition metal ions or combinations thereof;

$R^1$, $R^2$, $R^3$, $R^4$, $R^5$, $R^6$ and $R^7$ are each independently alkyl groups selected from a branched, cyclic or straight-chain hydrocarbon containing 1–12 carbon atoms, preferably 1–4 carbon atoms;

p is a number from 1–4;

m, d, q and t are each independently zero or 1 or more, preferably 1–5, such that the oligomer has a net positive charge; and r is a number from 0–100, or in the case of polymeric material may be greater than 100.

The alcoholic solution comprises a primary, secondary or tertiary alcohol, an alkoxyalkanol, an aminoalkanol, or a mixture thereof. In one embodiment, a non-inhibitory buffering agent is added to the solution to maintain the $_s^s$pH at the optimum range of $_s^s$pH, for example in the case of $La^{3+}$ in methanol, $_s^s$pH 7 to 11 (see FIG. 3). Examples of non-inhibitory buffering agents include: anilines; N-alkylanilines; N,N-dialkylanilines; N-alkylmorpholines; N-alkylimidazoles; 2,6-dialkylpyridines; primary, secondary and tertiary amines such as trialkylamines; and their various derivatives.

In another embodiment, non-inhibitory buffering agents are not added, but additional alkoxide ion is added in the form of an alkoxide salt to obtain metal ions and alkoxide ions in a metal:alkoxide ratio of about 1:0.01 to about 1:2, for some embodiments preferably about 1:1 to about 1:1.5, for other embodiments preferably about 1:0.5 to about 1:1.5. A person skilled in the art will recognize that an alcoholic solution contains trace amounts of alkoxide ions. This concept is analogous to water containing a trace amount of hydrogen ions and hydroxide ions, thus water of pH 7 contains, by definition, $[H^+]=1\times10^{-7}$ M and $[OH^-]=1\times10^{-7}$ M. For this reason, when alkoxide salts are added according to this embodiment of the invention, they are referred to as "additional" alkoxide ions. Suitable non-inhibitory cations for the alkoxide salts include monovalent ions such as, for example, $Na^+$, $K^+$, $Cs^+$, $Rb^+$, $NR_4^+$ and $NR'R''R'''R''''^+$ (where R', R", R'", and R"" may be the same or different and may be hydrogen or substituted or unsubstituted alkyl or aryl groups) and divalent ions such as the alkali earth metals, and combinations thereof. In some instances such ions may prolong the life of a catalyst by bonding to and, for example, precipitating, an inhibitory product of organophosophonus decomposition, an example of which is $Ca^{2+}$ bonding to fluoride.

To obtain the metal ions, metal salts are added to the solution. Preferably, the metal ion is a non-radioactive lanthanide series metal ion. Suitable lanthanide series metal ions include, for example, $Ce^{3+}$, $La^{3+}$, $Pr^{3+}$, $Nd^{3+}$, $Sm^{3+}$, $Eu^{3+}$,$Gd^{3+}$, $Tb^{3+}$, $Dy^{3+}$, $Ho^{3+}$, $Er^{3+}$, $Tm^{3+}$ and $Yb^{3+}$ and combinations thereof or complexes thereof. Suitable non-lanthanide series metal ions include, for example, divalent transition metal ions such as, for example, $Cu^{2+}$, $Pd^{2+}$, $Pt^{2+}$, $Zn^{2+}$, and trivalent transition metal ions such as, for example, $Sc^{3+}$ and $Y^{3+}$, as well as combinations thereof or complexes thereof, including combinations/complexes of those with non-radioactive lanthanide series metal ions. While $La^{3+}$($_s^s$p$Ka^1$=7.8) has good catalytic efficacy from $_s^s$pH 7.3 to 10.3, other metal ions which have lower $_s^s$pKa values (for example $Ho^{3+}$ and $Eu^{3+}$ have $_s^s$p$Ka_1$ values of 6.6, while $Yb^{3+}$ has a $_s^s$p$Ka_1$ value of 5.3, Gibson et al. 2003) may be efficacious at lower $_s^s$pH.

An embodiment of the invention is a catalytic system comprising mixtures of metal ions, for example, mixtures of lanthanide series metal ions which would be active between the wide $_s^s$pH range of 5 to 11. Lanthanide series metal ions and alkoxide may form several species in solution, an example of which, species forming from $La^{3+}$ and methoxide is shown in the figures. In the case of $La^{3+}$, a dimer containing 1 to 3 alkoxides is a particularly active catalyst for the degradation of organophosphorus compounds. In the case of non-lanthanide series metal ions, such as, for example $Zn^{2+}$ and $Cu^{2+}$, a mononuclear complex containing alkoxides is an active catalyst for the degradation of organophosphorus compounds.

In some embodiments, the invention provides limiting of dimerization and prevention of further oligomerization by addition of ligand such as, for example, bidentate and tridentate ligands. By coordination at one or more sites on a metal, a ligand limits dimerization and prevents further oligomerization of a metal species, thus allowing a greater number of active mononuclear species than is the case in the absence of ligand. Although not meant to be limiting, examples of such ligands are 2,2'-bipyridyl ("bpy")), 1,10-phenanthryl ("phen")), 2,9-dimethylphenanthryl ("diMe-phen")) and 1,5,9-triazacyclododecyl ("[12]ane$N_3$"), crown ether, and their substituted forms. Such ligands may be attached via linkages to solid support structures such as polymers, silicates or aluminates to provide solid catalysts for the alcoholysis of organophosphorus compounds which are decomposed according to the invention. The point of attachment of the metal:ligand:alkoxide complex to the solid support is preferably at the 3 or 4 position in the case of bipyridyl or the 3, 4 or 5 position in the case of phenanthrolines using linking procedures and connecting spacers which are known in the art. In the case of aza ligands, such as, for example, [12]ane$N_3$, the point of attachment of the complex to the solid support would preferably be on one of the nitrogens of the macrocycle, using methods and connecting spacers known in the art. Such attachment to solid supports offers advantages in that the solid catalysts may be conveniently recovered from the reaction media by filtration or decantation. In an embodiment of the invention wherein ligands are attached to solid support structures, organophosphorus compounds may be decomposed by running a solution through a column such as a chromatography column. In another embodiment of the invention wherein ligands are attached to solid support structures, organophosphorus compounds may be decomposed by contact with a polymer comprising metal species and alkoxide ions.

Suitable anions of the metal salts are non-inhibitory or substantially non-inhibitory and include, for example, $ClO_4^-$, $BF_4^-$, $BR_4^-I^-$, $Br^-$, $CF_3SO_3^-$(also referred to herein as"triflate" or "OTf") and combinations thereof. Preferred anions are $ClO_4^-$ and $CF_3SO_3^-$. In the case of $BF_4^-$, a solvent other than methanol is preferred.

The solution comprises solvents, wherein preferred solvents are alcohols, including primary and secondary alcohols such as methanol, ethanol, n-propanol, iso-propanol, n-butanol, 2-butanol and methoxyethanol, and combinations thereof. Most preferably the solution is all alcohol or all alkoxyalkanol or all aminoalkanol; however, combinations with non-aqueous non-inhibitory solvents can also be used, including, for example, nitriles, ketones, amines, ethers, hydrocarbons including chlorinated hydrocarbons and esters. In the case of esters, it is preferable that the alkoxy group is the same as the conjugate base of the solvent alcohol. In some embodiments, esters may cause side reactions which may be inhibitory.

Initial studies have been undertaken in methanol since methanol is closest to water in terms of structure and chemical properties and is readily available. However, methanol is less desirable than other solvents due to its toxicity and its relatively low boiling point of 64.7° C. which makes it volatile and prone to evaporation from open vessels. For these reasons, use of higher alcohols such as ethanol, n-propanol and iso-propanol has been explored (see Examples 1 and 2). Ethanol, n-propanol and iso-propanol are substantially less volatile (boiling points 78, 97.2 and 82.5° C. respectively), are less toxic, and have better solubilizing characteristics for hydrophilic substrates. The higher boiling points mean that these solvents are more amenable to field conditions since there would conveniently be less evaporation and thus less solvent would be lost to the atmosphere.

Other preferred solvents include n-butanol and 2-butanol since they have higher boiling points than the lower alcohols.

In accordance with the invention, the metal ion species catalyzes an alcoholysis reaction of an organophosphorus compound or a mixture of organophosphorus compounds represented by the following general formula (10):

(10)

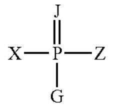

where P is phosphorus;

J is O (oxygen) or S (sulfur);

X, G, Z are the same or different and are selected from the group consisting of Q, OQ, QA, OA, F (fluoride), Cl (chloride), Br (bromide), I (iodide), QS, SQ and C≡N;

where Q is hydrogen or a substituted or unsubstituted branched, straight-chain or cyclic alkyl group consisting of 1–100 carbon atoms; wherein when X, G, Z are the same, X, G, Z are not Q, and when X, G, Z are the same Q is not H;

A is a mono-, di-, or poly-substituted or unsubstituted aryl group selected from phenyl, biphenyl, benzyl, pyridine, naphthyl, polynuclear aromatics, and 5- and 6-membered aromatic and non-aromatic heterocycles;

wherein each said substituent is selected from Cl, Br, I, F, nitro, nitroso, Q, alkenyl, OQ, carboxyalkyl, acyl, $SO_3H$, $SO_3Q$, S═O(Q), S(═O)$_2$Q, amino, alkylamino (NHQ), arylamino (NHA), alkylarylamino, dialkylamino and diarylamino.

Most preferably, the phosphorus atom of FIG. 10 has at least one good leaving group attached. For this reason, organophosphorus compounds which are decomposed according to the invention do not have three alkyl groups, nor three hydrogens, nor three hydroxyl groups attached. One skilled in the art will recognize that a "good leaving group" is a substituent with an unshared electron pair that readily departs from the substrate in a nucleophilic substitution reaction. The best leaving groups are those that become either a relatively stable anion or a neutral molecule when they depart, because they cause a stabilization of the transition state. Also, leaving groups that become weak bases when they depart are good leaving groups. Good leaving groups include halogens, alkanesulfonates, alkyl sulfates, and p-toluenesulfonates.

As used herein, the term "heterocycle" means a substituted or unsubstituted 5- or 6-membered aromatic or non-aromatic hydrocarbon ring containing one or more O, S or N atoms, or polynuclear aromatic heterocycle containing one or more N, O, or S atoms.

An advantage of the decomposition method of the invention is that the solvent, being hydrophobic, relative to water, permits good solubility of organophosphorus agents such as VX, Russian-VX, tabun (GA), soman (GD), sarin (GB), GF, hydrophobic polymers, insecticides and pesticides.

Another advantage of the invention is that it provides a non-aqueous solution and reaction products that can be easily and safely disposed of by incineration. It will thus be appreciated that the decontamination method of the invention can be used for a broad range of chemical warfare agents, or mixtures of such agents, or blends of such agents with polymers, as well as other toxic compounds such as insecticides, pesticides and related organophosphorus agents in general.

A further advantage of the invention is that destruction of organophosphorus agents occurs with or without the addition of heat. An ambient temperature reaction is cost-efficient for large scale destruction of stockpiled organophosphous material such as chemical weapons, insecticides or pesticides. The catalyst species can catalyze the alcoholysis over the full temperature range between the freezing and boiling points of the solvents or mixture of solvents used.

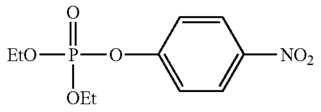

Paraoxon

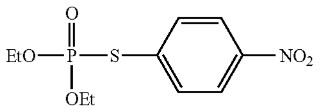

O,O'-diethyl-S-p-nitrophenylphosphothioate

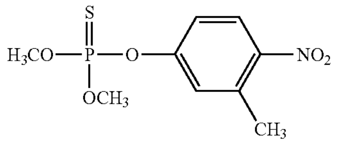

Fenitrothion

The G-type and V-type classes of chemical warfare agents are too toxic to be handled without specialized facilities and are often modeled by simulants such as, for the G-agents: paraoxon and p-nitrophenyl diphenyl phosphate, and for the V-agents: O,S-dialkyl- or O,S-arylalkyl-phosphonothioates or S-alkyl-phosphinothioates or S-aryl-phosphinothioates (Yang, 1999). We have used three such simulants and report herein, degradation of paraoxon as a model of G-agents, degradation of O,O'-diethyl-S-p-nitrophenylphosphorothioate as a model of V-agents, and degradation of fenitrothion as a model of (P═S)-containing pesticides. Structures for these model compounds are shown below. These three compounds were chosen because each possess a chromophore which makes the UV-vis kinetics simpler to study with low concentrations of materials. It is expected that this invention has wide applicability for other organophosphorus compounds including chemical warfare agents and other pesticides such as, for example, parathion and malathion.

In our studies, which are detailed in the following examples, we have: confirmed the degradation of paraoxon, O,O'-diethyl-S-p-nitrophenylphosphorothioate and fenitrothion when placed in an alcoholic solution of metal ions and at least a trace amount of alkoxide ions; determined the rate of the decomposition of paraoxon in a methanol solution containing $La^{3+}$ and additional methoxide ions; characterized stoichiometry and proposed a structure of active $\{La^{3+}(^-OCH_3)\}_2$ dimers; studied catalyzed alcoholysis in the presence of ligand and determined that faster rates are possible in some such systems relative to catalysis in the absence of ligand; and confirmed the complete destruction of paraoxon and O,O'-diethyl-S-p-nitrophenylphosphorothioate relative to catalyst in $\{La^{3+}$:$^-$OMe$\}$, $\{Cu^{2+}$:$^-$OMe$\}$, and $\{Zn^{2+}$, :$^-$OMe$\}$ systems thus confirming the true catalytic nature of this method.

The data presented in the following examples support the following conclusions:

Destruction of Paraoxon (Model G Agent): A preferred embodiment for methanolysis of paraoxon is a {$La^{3+}$:$^{-}OCH_3$} system according to the invention. The procedure involves preparation of a 2 mM $La(OTf)_3$ methanolic solution, containing equimolar $NaOCH_3$ which affords a $10^9$-fold acceleration of the methanolysis of paraoxon relative to the background reaction at the same $_s^s$pH in the absence of catalyst ($t_{1/2}$~20 sec). A second preferred embodiment for the methanolysis of paraoxon is a {$Zn^{2+}$:diMephen:$^{-}$OMe} system. This system affords accelerations of up to $1.8\times10^6$-fold for the methanolysis of paraoxon and has broader applicability than $La^{3+}$ as $Zn^{2+}$ also catalyzes the decomposition of fenitrothion.

Destruction of O,O'-diethyl-S-p-nitrophenylphosphorothioate (Model V Agent):

A preferred embodiment for methanolysis of O,O'-diethyl-S-p-nitrophenylphosphorothioate is a {$Cu^{2+}$:$^{-}OCH_3$:[12]andN$_3$} system. A second preferred embodiment for the methanolysis of O,O'-diethyl-S-p-nitrophenylphosphorothioate is methanolic solution of {$Zn^{2+}$:diMephen:-$OCH_3$}. A third preferred embodiment for the methanolysis of O,O'-diethyl-S-p-nitrophenylphosphorothioate is a methanolic solution of {$La^{3+}$:$^{-}OCH_3$}.

Destruction of Fenitrothion (Model Pesticide): A preferred embodiment for methanolysis of fenitrothion is a {$Cu^{2+}$:[12]aneN$_3$:$^{-}OCH_3$} system according to the invention. The procedure involves preparation of a 2 mM $Cu(OTf)_2$ methanolic solution containing 0.5 equivalents of $N(Bu)_4OCH_3$ and 1 equivalent of [12]aneN$_3$ which catalyzes the methanolysis of fenitrothion with a $t_{1/2}$ of ~58 sec accounting for a $1.7\times10^9$-fold acceleration of the reaction at near neutral $_s^s$pH (8.75). A second preferred embodiment for the methanolysis of fenitrothion is a {$Zn^{2+}$:diMephen:$^{-}OCH_3$} system. This system affords accelerations of $13\times10^6$-fold for the methanolysis of fenitrothion at 2 mM each of $Zn(OTf)_2$, ligand diMephen and $NaOCH_3$ and exhibits broad applicability as it also catalyzes the decomposition of paraoxon. Fenitrothion decomposition is not appreciably accelerated in the presence of a $La^{3+}$ system according to the invention. This points out the importance of matching the relative hard/soft characteristics of catalyst and substrate, and suggests that softer metal ions such as $Cu^{2+}$ and $Pd^{2+}$ could show enhanced catalytic activity toward the methanolysis of sulfur-containing phosphorus species.

Destruction of a Suspected Organophosphorus Compound of Unknown Structure: A preferred embodiment of the invention for catalyzed alcoholysis of an unknown agent which is suspected to be an organophosphorus compound, is a mixture of {$M^{3+}$:$^{-}OCH_3$} and {$M^{2+}$:L: $^{-}OCH_3$} in an alcohol solution. Examples of such a mixture include {$La^{3+}$:$OCH_3$} and {$Cu^{2+}$:[12]aneN$_3$:$OCH_3$}; and {$La^{3+}$:$OCH_3$} and {$Zn^{2+}$:diMephen:$OCH_3$}. Although such a $M^{2+}$ system is less reactive toward paraoxon than the $M^{3+}$ system; unlike $M^{3+}$, the $M^{2+}$ system does catalyze alcoholysis of fenitrothion. This mixture produces an effective method for destruction of both P═S pesticides and P═O chemical warfare agents.

The invention also provides a kit for decomposing an organophosphorus compound comprising a substantially non-aqueous medium for an alcoholysis reaction, said medium comprising-non-radioactive metal ions and at least a trace amount of alkoxide ions . The kit may include a container, e.g., an ampule, which is opened so that the medium can be applied to the organophosphorus compound. Alternatively, the kit may include an applicator bearing the medium, wherein the applicator is adapted so that the medium is applied to the organophosphorus compound and the compound consequently decomposes. The applicator may comprise a moist cloth, i.e., a cloth bearing a solution according to the invention. The applicator may be a sprayer which sprays medium according to the invention on the organophosphous compound. In some embodiments, the kit comprises written instructions for use to decompose an organophosphorus compound.

The following examples further illustrate the present invention and are not intended to be limiting in any respect. All scientific and patent publications cited herein are hereby incorporated by reference in their entirety.

EXAMPLES

Examples 5 to 8 provide a summary of the $La^{3+}$ ion catalyzed alcoholysis of paraoxon. Example 10 is a prophetic example of an $La^{3+}$ ion catalyzed alcoholysis of VX. Due to the fact that the dimeric lanthanum methoxide catalyst is stable in solution, and the reaction takes place at room temperature and at neutral pH (neutral $_s^s$pH in methanol is ~8.4), we expect that this reaction is amenable to scale-up and to use in the field.

In the examples, methanol (99.8% anhydrous), sodium methoxide (0.5 M solution in methanol), $La(CF_3SO_3)_3$ and paraoxon were purchased from Sigma-Aldrich (St. Louis, Mo.) and used without any further purification. $HClO_4$ (70% aqueous solution) was purchased from BDH (Dorset, England). $^1H$ NMR and $^{31}P$ NMR spectra were determined at 400 MHz and 161.97 MHz. $^{31}P$ NMR spectra were referenced to an external standard of 70% phosphoric acid in water, and up-field chemical shifts are negative.

In the examples, the $CH_3OH_{2+}$ concentration was determined using a Radiometer Vit 90 Autotitrator, equipped with a Radiometer GK2322 combination (glass/calomel) electrode calibrated with Fisher Certified Standard aqueous buffers (pH=4.00 and 10.00) as described in recent papers (Neverov et al 2000; Neverov et al., 2001 (a); Neverov et al., 2001(b); Neverov et al., 2001 (c); Brown et al., 2002; Tsang et al., 2003). Values of $_s^s$pH were calculated by adding a correction constant of 2.24 to the experimental meter reading as reported by Bosch et al., 1999.

The $_s^s pK_a$ values of buffers used in the examples were obtained from the literature or measured at half neutralization of the bases with 70% $HClO_4$ in MeOH.

Example 1

$M^{n+}$-Catalyzed Ethanolysis of Paraoxon and Fenitrothion: Reaction Conditions and Rates The ethanolysis of fenitrothion and paraoxon was studied in ethanol using various metal ions with varying amounts of added base. These reactions were followed by UV-vis spectroscopy by observing the rate of disappearance of a starting material signal or the rate of appearance of a product signal such as 4-nitrophenol in the case of paraoxon or 3-methyl-4-nitrophenol in the case of fenitrothion. Reaction conditions and the catalyzed reaction's rate constants are summarized in Table 1.

TABLE 1

Maximum pseudo-first order kinetic rate constants for the ethanolysis of fenitrothion and paraoxon catalyzed by metal ions (0.001 M) in the presence of optimum amount of base (max $k_{obs}$) and at equimolar amount ($k_{obs}$ 1:1 $OCH_3/M^x$ ratio), T = 25° C.

| | Paraoxon | | Fenitrothion |
|---|---|---|---|
| Metals[a] | $10^4$ Max $k_{obs}$, $s^{-1}$ | $10^4$ $k_{obs}$, $s^{-1}$ [b] | $10^4$ $k_{obs}$, $s^{-1}$ [b] |
| Lanthanides | | | |
| $La^{3+}$ | 544.15 (1:1) | 544.15 | No catalysis |
| $Pr^{3+}$ | 253.24 (1:1) | 253.24 | No catalysis |
| $Nd^{3+}$ | 247.59 (1:1) | 247.59 | No catalysis |
| $Gd^{3+}$ | 220.14 (1:1) | 220.14 | No catalysis |
| $Sm^{3+}$ | 185.88 (1:1) | 185.88 | No catalysis |
| $Eu^{3+}$ | 160.0 (1:1) | 160 | No catalysis |
| $Tb^{3+}$ | 146.34 (1:1) | 146.34 | No catalysis |
| $Ho^{3+}$ | 99.72 (1:1) | 99.72 | No catalysis |
| $Dy^{3+}$ | 63.65 (1:1) | 63.65 | No catalysis |
| $Er^{3+}$ | 62.61 (1:1) | 62.61 | No catalysis |
| $Tm^{3+}$ | 49.34 (1:1) | 49.34 | No catalysis |
| Transition Metals | | | |
| $Zn^{2+}$ | 48.22 (1:0:5) | 37.28 | 5.42 |
| $Y^{3+}$ | 32.56 (1:1) | 32.56 | No catalysis |
| $Co^{2+}$ | 25.70 (1:0:5) | Catalysis, rate unknown[c] | Catalysis, rate unknown[c] |
| $Yb^{3+}$ | 25.73 (1:1) | 25.73 | No catalysis |
| $Ni^{2+}$ | 23.63 (1:0:5) | 12.18 | No catalysis |
| $Cu^{2+}$ | No catalysis | No catalysis | Catalysis, rate unknown[c] |
| $Sc^{3+}$ | No catalysis | No catalysis | No catalysis |

[a]Introduced as commercially available triflate salts and used as received
[b]0.001 M in each of $M^{n+}$ salt and added $NaOCH_3$
[c]Product formation was observed by final UV-vis spectra, but determination of exact value of the rate constant was not possible due to high absorbance of the solutions.

Example 2

$La^{3+}$ and $Zn^{2+}$-Catalyzed Solvolysis of Paraoxon in Propanols: Kinetics and NMR Studies The solvolysis of paraoxon was studied in two alcohols that are less polar than methanol, namely 1-propanol and 2-propanol. In the case of 1-propanol, kinetics were monitored by UV-vis spectroscopic techniques following the appearance of the product of the solvolysis, 4-nitrophenol, at λ=335 nanometers. For example, at a concentration of $La(OTf)_3$=0.5 mM=concentration of $NaOCH_3$, in the absence of any ligand, catalyzed solvolysis of paraoxon proceeded with a pseudo-first order rate constant of $2.1\times10^{-4}$ $s^{-1}$. At a concentration of $Zn(OTf)_2$=0.5 mM=concentration of $NaOCH_3$, in the presence of equimolar diMephen, the catalyzed solvolysis of paraoxon proceeded with a pseudo-first rate constant of $1.93\times10^{-4}$ $s^{-1}$.

The true catalytic nature of the system was demonstrated in the following Nuclear Magnetic Resonance (NMR) studies. To 2.5 mL of a solution of 1-propanol containing 5% methanol, and 0.5 mM each of $Zn(OTf)_2$, diMephen and NaOMe was added 8.3 μL of paraoxon so that the latter's total concentration was 15.4 mM. The alcoholic solution was then incubated at room temperature for 72 hours after which the $^{31}P$ NMR spectrum was recorded. This spectrum showed complete disappearance of the paraoxon starting material and complete formation of diethyl methyl phosphate (product of reaction with methanol) (δ=−0.3 ppm) and diethyl 1-propyl phosphate (product of reaction with 1-propanol) (δ=−1.23 ppm). This indicates true catalysis with more than 30 turnovers in 72 hr. The solvents were removed, and the residues dissolved in deuterated methanol-$d_4$ and the $^1H$ NMR spectra were recorded showing the presence of the products: 4-nitrophenol, diethyl methyl phosphate and diethyl 1-propyl phosphates. Similarly, an NMR study was done such that 2.5 mL of 2-propanol containing 5% methanol, 0.5 mM each of $Zn(OTf)_2$, diMephen and NaOMe was added 8.3 μL of paraoxon so that the latter's total concentration was 15.4 mM. The alcoholic solution was then incubated at room temperature for 72 hours after which the $^{31}P$ NMR spectrum was recorded. This spectrum showed complete disappearance of the paraoxon starting material and complete formation of diethyl methyl phosphate (product of reaction with methanol) (δ=−0.3 ppm) and diethyl 2-propyl phosphate (product of reaction with 2-propanol) (δ=−2.4ppm) was observed and formation of the products 4-nitrophenol, diethyl methyl phosphate and diethyl 2-propyl phosphate were confirmed by $^1H$ NMR.

The ratio of the two phosphate products from each of the propanol solvents was determined from their $^{31}P$ NMR spectra and were found to be:

| | MeOH reaction product: Propanol reaction product |
|---|---|
| 1-propanol reaction | 1:2.8 |
| 2-propanol reaction | 2.2:1. |

These ratios show that if the medium for catalysis according to the invention is a mixture of alcohol, alkoxyalkanol and aminoalkanol, the reaction will select for the least hindered one. This factor may determine what an "effective amount" of methanol will be for a given system.

Example 3

$La^{3+}$-Catalyzed Methanolysis of Paraoxon: Experimental Details

Paraoxon, when placed in an appropriately buffered methanol solution containing $La^{3+}$ions held in a ${}_s^s$pH region between 7 and 11, underwent rapid methanolysis at ambient temperature to produce diethyl methyl phosphate and p-nitrophenol. A detailed reaction scheme is given in Scheme 1.

Scheme 1

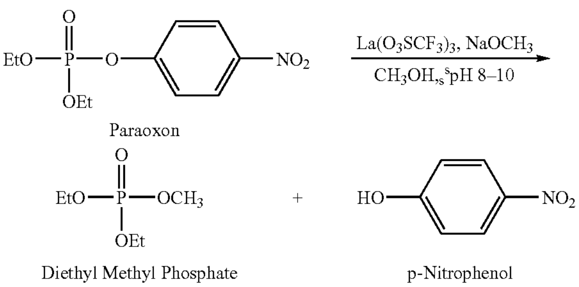

Paraoxon

Diethyl Methyl Phosphate p-Nitrophenol

To two mL of dry methanol at ambient temperature was added N-ethylmorpholine (25.5 μL or 23 mg) half neutralized with 11.4 M HClO4 (8.6 μL) so that the final total buffer concentration was 0.1 M. To this was added 16.0 mg of paraoxon. The $^{31}P$ NMR spectrum showed a single signal at δ-6.35 ppm. To the resulting mixture was added 12.9 mg of $La(O_3SCF_3)_3$ and 40 μL of 0.5 M $NaOCH_3$ in methanol solution. At this point the concentration of paraoxon was 0.057 M and that of $La(O_3SCF_3)_3$ was 0.011 M and the measured $_s^s$pH of the methanol solution was 8.75, essentially neutrality. This solution was allowed to stand for 10 minutes, after which time the $^{31}$P NMR spectrum indicated complete disappearance of the paraoxon signal and the appearance of a new signal at δ 0.733 ppm corresponding to diethyl methyl phosphate. The $^1$H NMR spectrum indicated complete disappearance of the starting material and full release of free p-nitrophenol.

Example 4

$La^{3+}$-Catalyzed Methanolysis of G-agent: A Prophetic Example

To 200 mL of methanol is added 2.55 mL of N-ethylmorpholine (2.3 g) and 0.86 mL of 11.4 M $HClO_4$ to bring the total buffer concentration to 0.1 M. To this solution is added 1.29 g of $La(O_3SCF_3)_3$ and 4 mL of a 0.5 M solution of $NaOCH_3$ in methanol.

To the above solution is added 2 g of the G-agent Sarin (0.016 moles, 0.08 M) and the solution is allowed to stand at ambient temperature for 15 minutes. It is expected that analysis of the resulting solution would indicate substantially complete disappearance of Sarin. This reaction may be inhibited by F in which case $Ca^{2+}$ may be added to the reaction solution to precipitate this inhibitory product.

Example 5

$La^{3+}$-Catalyzed Methanolysis of Paraoxon: Kinetics

The kinetics of the alcoholysis degradation reaction have been thoroughly investigated using the pesticide paraoxon. For methanolysis with dimeric lanthanum catalysts at 25° C., as little as $10^{-3}$ M of the catalytic specie(s) promotes the methanolysis reaction by ~$10^9$-fold relative to the background reaction at a neutral $_s^s$pH of ~8.5. The uncatalyzed methoxide-promoted reaction of paraoxon proceeds with the second order rate constant, $k_2^{OCH3}$ of 0.011 $M^{-s-1}$ determined from concentrations of $NaOCH_3$ between $1\times10^{-2}$ M and $4\times10^{-2}$ M. Methanolysis of paraoxon is markedly accelerated in the presence of $La^{3+}$ with an observed second order rate constant, $k_2^{obs}$ of ~17.5 $M^{-1}s^{-1}$ at the near neutral $_s^s$pH of 8.23. Assuming that the methoxide reaction persists at $_s^s$pH 8.23, the acceleration afforded to the methanolysis of paraoxon at that $_s^s$pH by a $2\times10^{-3}$ M solution of $La(O_3SCF_3)_3$ is $1.1\times10^9$-fold giving a half-life time of 20 seconds. The acceleration is $2.3\times10^9$-fold at $_s^s$pH 7.72 and $2.7\times10^8$-fold at $_s^s$pH 8.96.

UV kinetics of the methanolysis of paraoxon were monitored at 25° C. by observing the rate of loss of paraoxon at 268 nm or by the rate of appearance of p-nitrophenol at 313 nm or 328 nm at a concentration of paraoxon=$2.04\times10^{-5}$ M using an OLIS®-modified Cary 17 UV-vis spectrophotometer. The concentration of $La(O_3SCF_3)_3$ was varied from $8\times10^{-6}$ M to $4.8\times10^{-3}$ M. All reactions were followed to at least three half-times and found to exhibit good pseudo-first order rate behavior. The pseudo-first order rate constants ($k_{obs}$) were evaluated by fitting the Absorbance vs. time traces to a standard exponential model.

The kinetics were determined under buffered conditions. Buffers were prepared from N,N-dimethylaniline ($_s^s pK_a$=5.00), 2,6-lutidine ($_s^s pK_a$=6.70), N-methylimidazole ($_s^s pK_a$=7.60), N-ethylmorpholine ($_s^s pK_a$=8.60) and triethylamine ($_s^s pK_a$=10.78). Due to the fact that added counterions can ion-pair with $La^{3+}$ ions and affect its speciation in solution, ionic strength was controlled through neutralization of the buffer and not by added salts. The total concentration of buffer varied between $7\times10^{-3}$ M and $3\times10^{-2}$ M, and the buffers were partially neutralized with 70% $HClO_4$ to keep the concentration of $ClO_4^-$ at a low but constant value of $5\times10^{-3}$ M which leads to a reasonably constant ionic strength in solution. With the concentration of $La^{3+}$ >$5\times10^{-4}$ M at $_s^s$pH>7.0, the metal ion was partially neutralized by adding an appropriate amount of NaOMe to help control the $_s^s$pH at the desired value. $_s^s$pH measurements were performed before and after each experiment and in all cases the values were consistent to within 0.1 units.

Figure 2:
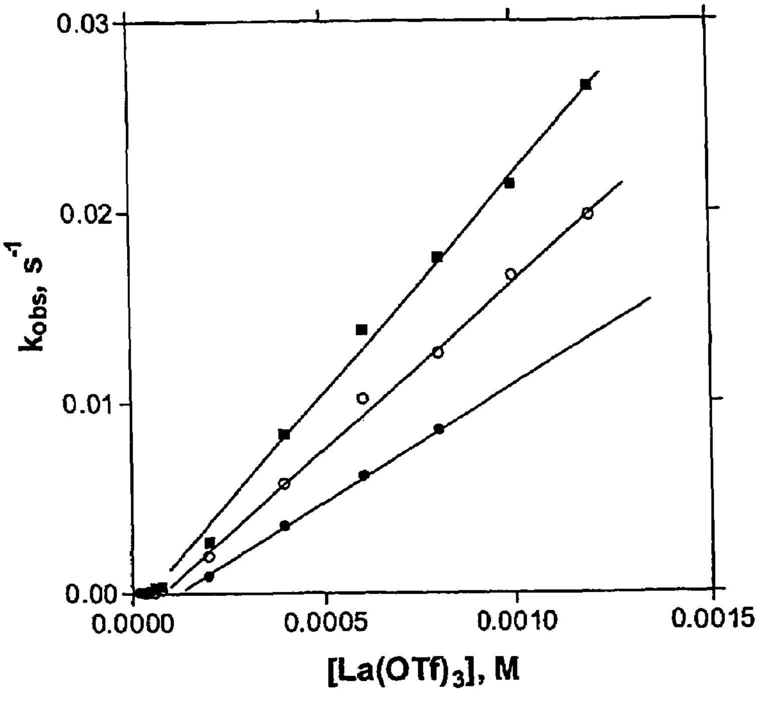
FIG. 2 shows a plot of $k_{obs}$ vs. concentration of $La(OTf)_3$ for the $La^{3+}$-catalyzed methanolysis of paraoxon ($2.04\times10^{-5}$ M) at 25° C., where ■, ${}_s^s$pH 8.96.

Shown in FIG. 2 are three representative plots of the pseudo-first order rate constants ($k_{obs}$) for methanolysis of paraoxon as a function of added concentration of $La(O_3SCF_3)_3$ at $_s^s$pH 7.72, 8.23 and 8.96. (For original $k_{obs}$ vs. concentration of $La^{3+}$ kinetic data see Tables 2–12).

TABLE 2

Observed pseudo-first order rate constants for $La^{3+}$ catalyzed methanolysis of paraoxon (2.04 × $10^{-5}$ M) at 25° C.; $_s^s$pH 5.15 [dimethylaniline buffer] = 1.00 × $10^{-2}$ M, λ = 328 nm.

| $La(O_3SCF_3)_3$, M | $k_{obs}$, $s^{-1}$ |
|---|---|
| 4.00E−05 | 3.11E−07 |
| 6.00E−05 | 5.46E−07 |
| 8.00E−05 | 4.90E−07 |
| 2.00E−04 | 1.17E−05 |
| 4.00E−04 | 2.46E−05 |
| 6.00E−04 | 3.78E−05 |
| 8.00E−04 | 5.34E−05 |
| 1.00E−03 | 6.13E−05 |
| 1.20E−03 | 7.72E−05 |

TABLE 3

Observed pseudo-first order rate constants for $La^{3+}$ catalyzed methanolysis of paraoxon (2.04 × $10^{-5}$ M) at 25° C.; $_s^s$pH 5.58 [dimethylaniline buffer] = 2.00 × $10^{-2}$ M, λ = 328 nm.

| $La(O_3SCF_3)_3$, M | $k_{obs}$, $s^{-1}$ |
|---|---|
| 4.00E−05 | 5.37E−06 |
| 6.00E−05 | 6.23E−06 |
| 8.00E−05 | 5.63E−06 |
| 2.00E−04 | 8.33E−06 |
| 4.00E−04 | 4.28E−05 |
| 6.00E−04 | 6.93E−05 |
| 8.00E−04 | 9.48E−05 |
| 1.00E−03 | 1.05E−04 |
| 1.20E−03 | 1.26E−04 |

TABLE 4

Observed pseudo-first order rate constants for $La^{3+}$ catalyzed methanolysis of paraoxon (2.04 × $10^{-5}$ M) at 25° C.; $_s^s$pH 5.82 [dimethylaniline buffer] = 2.93 × $10^{-2}$ M, λ = 328 nm.

| $La(O_3SCF_3)_3$, M | $k_{obs}$, $s^{-1}$ |
|---|---|
| 4.00E−05 | 1.15E−06 |
| 6.00E−05 | 1.71E−06 |
| 8.00E−05 | 2.52E−06 |
| 2.00E−04 | 3.13E−05 |
| 4.00E−04 | 7.11E−05 |

TABLE 4-continued

Observed pseudo-first order rate constants for $La^{3+}$ catalyzed methanolysis of paraoxon ($2.04 \times 10^{-5}$ M) at 25° C.; ${}_s^s$pH 5.82 [dimethylaniline buffer] = $2.93 \times 10^{-2}$ M, λ = 328 nm.

| $La(O_3SCF_3)_3$, M | $k_{obs}$, $s^{-1}$ |
|---|---|
| 6.00E−04 | 1.15E−04 |
| 8.00E−04 | 1.92E−04 |
| 1.00E−03 | 2.17E−04 |
| 1.20E−03 | 3.07E−04 |

TABLE 5

Observed pseudo-first order rate constants for $La^{3+}$ catalyzed methanolysis of paraoxon($2.04 \times 10^{-5}$ M) at 25° C.; ${}_s^s$pH 6.69 [2,6-Lutidine buffer] = $6.61 \times 10^{-3}$ M, λ = 313 nm.

| $La(O_3SCF_3)_3$, M | $k_{obs}$, $s^{-1}$ |
|---|---|
| 4.00E−05 | 1.18E−05 |
| 6.00E−05 | 3.13E−05 |
| 8.00E−05 | 4.43E−05 |
| 2.00E−04 | 1.21E−04 |
| 4.00E−04 | 3.04E−04 |
| 6.00E−04 | 5.24E−04 |
| 8.00E−04 | 8.00E−04 |
| 1.00E−03 | 9.31E−04 |
| 1.20E−03 | 1.18E−03 |

TABLE 6

Observed pseudo-first order rate constants for $La^{3+}$ catalyzed methanolysis of paraoxon($2.04 \times 10^{-5}$ M) at 25° C.; ${}_s^s$pH 7.10 [2,6-Lutidine buffer] = $1.00 \times 10^{-2}$ M, λ = 313 nm.

| $La(O_3SCF_3)_3$, M | $k_{obs}$, $s^{-1}$ |
|---|---|
| 4.00E−05 | 2.58E−05 |
| 6.00E−05 | 4.86E−05 |
| 8.00E−05 | 6.68E−05 |
| 2.00E−04 | 2.62E−04 |
| 4.00E−04 | 7.22E−04 |
| 6.00E−04 | 1.26E−03 |
| 8.00E−04 | 1.88E−03 |
| 1.00E−03 | 2.14E−03 |
| 1.20E−03 | 2.67E−03 |

TABLE 7

Observed pseudo-first order rate constants for $La^{3+}$ catalyzed methanolysis of paraoxon($2.04 \times 10^{-5}$ M) at 25° C.; ${}_s^s$pH 7.30 [N-methyimidazole buffer] = $6.67 \times 10^{-3}$ M, λ = 268 nm.

| $La(O_3SCF_3)_3$, M | $k_{obs}$, $s^{-1}$ |
|---|---|
| 8.00E−06 | 3.83E−05 |
| 2.00E−05 | 1.50E−05 |
| 8.00E−05 | 7.95E−05 |
| 2.00E−04 | 7.17E−04 |
| 4.00E−04 | 1.58E−03 |
| 8.00E−04 | 3.97E−03 |
| 1.60E−03 | 8.45E−03 |
| 3.20E−03 | 1.70E−02 |
| 4.80E−03 | 2.28E−02 |

TABLE 8

Observed pseudo-first order rate constants for $La^{3+}$ catalyzed methanolysis of paraoxon($2.04 \times 10^{-5}$ M) at 25° C.; ${}_s^s$pH 7.72 [N-methyimidazole buffer] = $1.00 \times 10^{-2}$ M, λ = 268 nm.

| $La(O_3SCF_3)_3$, M | $k_{obs}$, $s^{-1}$ |
|---|---|
| 2.00E−05 | 2.83E−06 |
| 8.00E−05 | 1.18E−04 |
| 2.00E−04 | 9.30E−04 |
| 4.00E−04 | 3.49E−03 |
| 6.00E−04 | 6.10E−03 |
| 8.00E−04 | 8.46E−03 |
| 1.20E−03 | 1.22E−02 |
| 1.60E−03 | 1.51E−02 |

TABLE 9

Observed pseudo-first order rate constants for $La^{3+}$ catalyzed methanolysis of paraoxon($2.04 \times 10^{-5}$ M) at 25° C.; ${}_s^s$pH 8.23 [N-methyimidazole buffer] = $2.00 \times 10^{-2}$ M, λ = 268 nm.

| $La(O_3SCF_3)_3$, M | $k_{obs}$, $s^{-1}$ |
|---|---|
| 4.00E−05 | 5.08E−05 |
| 6.00E−05 | 9.74E−05 |
| 8.00E−05 | 1.63E−04 |
| 2.00E−04 | 1.94E−03 |
| 4.00E−04 | 5.65E−03 |
| 6.00E−04 | 1.01E−02 |
| 8.00E−04 | 1.26E−02 |
| 1.00E−03 | 1.66E−02 |
| 1.20E−03 | 1.98E−02 |

TABLE 10

Observed pseudo-first order rate constants for $La^{3+}$ catalyzed methanolysis of paraoxon ($2.04 \times 10^{-5}$ M) at 25° C.; ${}_s^s$pH 8.96 [N-ethylmorpholine buffer] = $2.00 \times 10^{-2}$ M, λ = 268 nm.

| $La(O_3SCF_3)_3$, M | $k_{obs}$, $s^{-1}$ |
|---|---|
| 4.00E−05 | 8.50E−05 |
| 6.00E−05 | 2.03E−04 |
| 8.00E−05 | 3.75E−04 |
| 2.00E−04 | 2.70E−03 |
| 4.00E−04 | 8.25E−03 |
| 6.00E−04 | 1.38E−02 |
| 8.00E−04 | 1.76E−02 |
| 1.00E−03 | 2.14E−02 |
| 1.20E−03 | 2.65E−02 |

TABLE 11

Observed pseudo-first order rate constants for $La^{3+}$ catalyzed methanolysis of paraoxon ($2.04 \times 10^{-5}$ M) at 25° C.; ${}_s^s$pH 10.34 [triethythlamine buffer] = $6.67 \times 10^{-3}$ M, λ = 268 nm.

| $La(O_3SCF_3)_3$, M | $k_{obs}$, $s^{-1}$ |
|---|---|
| 4.00E−05 | 1.75E−04 |
| 6.00E−05 | 4.52E−04 |
| 8.00E−05 | 1.43E−03 |
| 2.00E−04 | 4.75E−03 |
| 4.00E−04 | 8.08E−03 |
| 6.00E−04 | 1.10E−02 |
| 8.00E−04 | 1.28E−02 |
| 1.00E−03 | 1.42E−02 |
| 1.20E−03 | 1.66E−02 |

TABLE 12

| Observed pseudo-first order rate constants for $La^{3+}$ catalyzed methanolysis of paraoxon ($2.04 \times 10^{-5}$ M) at 25° C.; ${}_s^s$pH 10.97 [triethylamine buffer] = $1.00 \times 10^{-2}$ M, λ = 268 nm. | |
|---|---|
| $La(O_3SCF_3)_3$, M | $k_{obs}$, $s^{-1}$ |
| 4.00E−05 | 1.60E−04 |
| 6.00E−05 | 3.98E−04 |
| 8.00E−05 | 5.21E−04 |
| 2.00E−04 | 3.49E−03 |
| 4.00E−04 | 5.42E−03 |
| 6.00E−04 | 6.23E−03 |
| 8.00E−04 | 7.57E−03 |
| 1.00E−03 | 8.17E−03 |
| 1.20E−03 | 9.15E−03 |

As was observed in our earlier studies of the $La^{3+}$-catalyzed methanolysis of esters (Neverov et al., 2001) and acetyl imidazole, (Neverov et al., 2000 & Neverov et al., 2001) these plots exhibit two domains, a nonlinear one at low eoncentration of $La^{3+}$ suggestive of a second order behavior in $La^{3+}$, followed by a linear domain at higher concentration of $La^{3+}$. Following the approach we have used before, (Neverov et al., 2001, Neverov et al., 2000 & Neverov et al., 2001) we use the linear portion of these plots to calculate the observed second order rate constants ($k_2^{obs}$) for $La^{3+}$-catalyzed methanolysis of paraoxon at the various ${}_s^s$pH values. These are tabulated in Table 13 and graphically presented in FIG. 3 as a log $k_2^{obs}$ vs. ${}_s^s$pH plot which is seen to have a skewed bell-shape, maximizing at ${}_s^s$pH ~9.

TABLE 13

| Observed second order rate constants for $La^{3+}$ catalyzed methanolysis of paraoxon at various ${}_s^s$pH values, T = 25° C. | |
|---|---|
| ${}_s^s$pH | $k_2^{obs}$, $M^{-1}$ $s^{-1}$ [a] |
| 5.15 | 0.065 ± 0.002 |
| 5.58 | 0.11 ± 0.01 |
| 5.82 | 0.28 ± 0.02 |
| 6.69 | 1.07 ± 0.04 |
| 7.10 | 2.4 ± 0.1 |
| 7.30 | 5.6 ± 0.1 |
| 7.72 | 11.3 ± 0.5 |
| 8.23 | 17.5 ± 0.5 |
| 8.96 | 23.2 ± 0.9 |
| 10.34 | 11.4 ± 0.8 |
| 10.97 | 5.4 ± 0.4 |

[a] $k_2$ determined from slope of the $k_{obs}$ vs. $[La^{3+}]_{total}$ plots at higher $[La^{3+}]$ at each ${}_s^s$pH.

Example 6

$La^{3+}$ Catalyst Species: Stoichiometries

As shown in FIG. 3, the reactivity of the catalytic species increases with increasing ${}_s^s$pH up to ~9.0. This fact seems to indicate the involvement of at least one methoxide, although the general shape of the plot suggests the catalytic involvement of more than one species. Since the second order $k_2^{obs}$ values for the $La^{3+}$-catalyzed reactions in the neutral ${}_s^s$pH region are some 1000- to 2300-fold larger than the methoxide $k_2^{OCH3}$, the role of the metal ion is not to simply decrease the ${}_s^s$p$K_a$ of any bound $CH_3OH$ molecules that act as nucleophiles. This points to a dual role for the metal, such as acting as a Lewis acid and as a source of the nucleophile.

Detailed mechanistic evaluation of kinetic data requires additional information such as the stoichiometries and concentrations of various $La^{3+}$-containing species that are formed as a function of both ${}_s^s$pH and concentration of $La^{3+}$. A study of the potentiometric titration of $La^{3+}$ was performed under various conditions, with the concentration of $La(O_3SCF_3)_3$ from $1\times10^{-3}$ M to $3\times10^{-3}$ M, which is within the concentration range where the kinetic plots of $k_{obs}$ vs. concentration of $La^{3+}$ in this study are linear. The potentiometric titration data were successfully analyzed with the computer program Hyperquad™ (Gans et a., 1996) through fits to the dimer model presented in equation(1) where n assumes values of 1–5, to give the various stability constants (${}_s^sK_n$) that are defined in equation(2). On the basis of the five computed stability constants, log ${}_s^sK_{1-5}$=11.66±0.04, 20.86±0.07, 27.52±0.09, 34.56±0.20 and 39.32±0.26, we constructed the speciation diagram shown in FIG. 4 which presents the distribution of the various $La_2(OCH_3)_n$ forms as a function of ${}_s^s$pH at $[La(O_3SCF_3)_3]_{total}$=$2\times10^{-3}$ M.

$$La^{3+}{}_2({}^-OMe)_n \underset{}{\overset{{}_s^sK_n}{\rightleftharpoons}} 2La^{3+} + n\,OMe^- \quad (1)$$

$${}_s^sK_n=[La^{3+}{}_2(OCH_3)_n]/[La^{3+}]^2[OCH_3^-]^n \quad (2)$$

Also included on FIG. 4 as data points (•) are the $k_2^{obs}$ data for $La^{3+}$-catalyzed methanolysis of paraoxon which predominantly coincide with the ${}_s^s$pH distribution of $La^{3+}{}_2(OCH_3)_2$ but with an indication that higher order species such as $La^{3+}{}_2(OCH_3)_3$ and/or $La^{3+}{}_2(OCH_3)_4$ have some activity. To determine the activities for the various $La^{3+}{}_2(OCH_3)_n$ we analyzed the $k_2^{obs}$ data as a linear combination of individual rate constants (equation(3).

$$k_2^{obs}=(k_2^{2:1}[La^{3+}{}_2(OCH_3)_1]+k_2^{2:2}[La^{3+}{}_2(OCH_3)_2]+\ldots k_2^{2:n}[La^{3+}{}_2(OCH_3)_n])/[La^{3+}(O_3SCF_3)_3]_{total} \quad (3)$$

where $k_2^{2:1}$, $k_2^{2:2}$, . . . . $k_2^{2:n}$ are the second order rate constants for the methanolysis of paraoxon promoted by the various dimeric forms. Given in Table 14 are the best-fit rate constants produced by fitting under various assumptions.

TABLE 14

Computed second order rate constants for various dimeric forms $La_2(OCH_3)_n$, catalyzing the methanolysis of paraoxon, as determined from fits of $k_2^{obs}$ data in Table 13 to equation(3), $[La(O_3SCF_3)_3]_{total} = 2 \times 10^{-3}$ M, T = 25° C.

| Fit # | $K_2^{2:1}$ ($M^{-1}s^{-1}$) | $K_2^{2:2}$ ($M^{-1}s^{-1}$) | $K_2^{2:3}$ ($M^{-1}s^{-1}$) | $K_2^{2:4}$ ($M^{-1}s^{-1}$) | $R^2$ |
|---|---|---|---|---|---|
| 1[a] | 15.9 ± 3.2 | 49.8 ± 2.2 | 67.2 ± 36.0 | 8.8 ± 11.2 | 0.9976 |
| 2[b] | 18.4 ± 5.4 | 47.2 ± 2.4 | 110.4 ± 11.8 | — | 0.9861 |
| 3[c] | — | 51.4 ± 2.8 | 103.4 ± 17 | — | 0.9664 |

[a]Including all dimeric forms except $La_2(OCH_3)_0$ and $La_2(OCH_3)_6$. Computed value of $k^{2:5}$ = (−3.4 ± 10.8) $M^{-1}s^{-1}$.
[b]Computed without the involvement of $k_2^{2:4}$ and $k_2^{2:5}$.
[c]Computed without the involvement of $k_2^{2:1}$, $k_2^{2:4}$ and $k_2^{2:5}$.

We have analyzed the titration data to determine speciation for a total $La^{3+}$ concentration of $2\times10^{-3}$ M which is in the general concentration range where the kinetic behavior of the methanolysis of paraoxon is linearly dependent on concentration of $La^{3+}$, and thus largely controlled by dimeric species. In FIG. 5 are presented kinetic plots for all three species ($La^{3+}{}_2(OCH_3)_1$, $La^{3+}{}_2(OCH_3)_2$ and $La^{3+}{}_2(OCH_3)$) rate constants for catalyzed methanolysis of paraoxon, and their concentrations as a function of ${}_s^s$pH. Their combined reactivities as a function of ${}_s^s$pH give the predicted log $k_2^{obs}$ vs. ${}_s^s$pH profile shown as the dashed line on FIG. 5. The computed line is also presented in the plot in FIG. 2 of log $k_2^{obs}$ vs. ${}_s^s$pH. Included on FIG. 5 as data points (■)■are the actual experimentally-determined values which fit on the computed profile with remarkable fidelity, strongly indicating that these three species are responsible for the observed activity. At ${}_s^s$pH values below 9, the $La^{3+}{}_2(OCH_3)_2$ complex accounts for essentially all the activity, while at ${}_s^s$pH 10 and above, the dominantly active form is $La^{3+}{}_2(OCH_3)_4$.

Through joint consideration of the $k_{obs}$ vs. concentration of $La^{3+}$ kinetics and a detailed analysis of the potentiometric titration data for $La^{3+}$ in methanol, we have determined that the dominant species in solution are dimers of the general formula $La_2(OCH_3)_n$ where n=1–5, and three of these dimers, $La^{3+}{}_2(OCH_3)_1$, $La^{3+}{}_2(OCH_3)_2$ and $La^{3+}{}_2(OCH_3)_3$, account for all the catalytic activity with $La^{3+}{}_2(OCH_3)_2$ being the most important form at ${}_s^s$pH<9.

The ${}_s^s$pH dependence of the metal ion is such that several complexes are present with their individual concentrations maximized at different ${}_s^s$pH values. It is only through complementary analyses of the kinetic and potentiometric titration data that one can satisfactorily explain the kinetic behavior of complex mixtures having several ${}_s^s$pH dependent forms.

Through a series of detailed potentiometric titrations of the {$La^{3+}$:$^-$OMe} system in methanol, and through studies of the kinetics of methanolysis of paraoxon as a function of $La^{3+}$ concentration and ${}_s^s$pH, it has been determined that in this {$La^{3+}$:$^-$OMe:paraoxon} system there are two dominant stoichiometries of catalysts, $La_2(OCH_3)_2$ with a proposed structure of a bis-methoxy bridged dimer between ${}_s^s$pH 8 and 10 (maximum concentration of ~80% at ${}_s^s$pH 8.9), and $La_2(OCH_3)_3$ with a proposed structure of tris-methoxy bridged dimer) between ${}_s^s$pH 9 and 11 (maximum concentration of ~25% at ${}_s^s$pH 10). Above a total [$La^{3+}$] of about $2\times10^{-4}$ M, these species form spontaneously in solution without any requirement for added ligands, so that in the millimolar concentration range, dimer formation is essentially complete.

Given that we know the dominantly active forms are $La^{3+}{}_2(OCH_3)_2$ and $La^{3+}{}_2(OCH_3)_3$, we can derive a kinetic expression (equation4) which gives values of $k_2^{2:2}$=51.4±2.8 and $k_2^{2:3}$=103±17 $M^{-1}s^{-1}$ for the second order rate constants for methanolysis of paraoxon catalyzed by the bis-methoxy dimer and the tris-methoxy dimer respectively (Table 14).

$$\text{i } k_2^{obs}=k_2^{2:2}[La^{3+}{}_2(OCH_3)_2]+k_2^{2:3}[La^{3+}{}_2(OCH_3)_3] \quad (4)$$

The net effect of this is that a solution containing $2\times10^{-3}$ M of $La(OTf)_3$, generating $1\times10^{-3}$ M of total dimer, will catalyze the methanolysis of paraoxon with $t_{1/2}$ values of 30s, 20s, 15s and 30s at respective ${}_s^s$pH values of 7.7, 8.2, 9.0 and 10.3. By way of reference, at ${}_s^s$pH 7.7 the methoxide background rate constant is (0.011 $M^{-1}s^{-1}\times10^{-9}$ M [$OCH^{3-}$])=$1.1\times10^{-11}$ $s^{-1}$, corresponding to a $t_{1/2}$ of 1994 years, so that the acceleration afforded by the $La^{3+}$ catalyst is some two billion-fold at that ${}_s^s$pH.

Example 7

$La^{3+}$ Catalysis: Proposed Mechanism

Figure 1A:
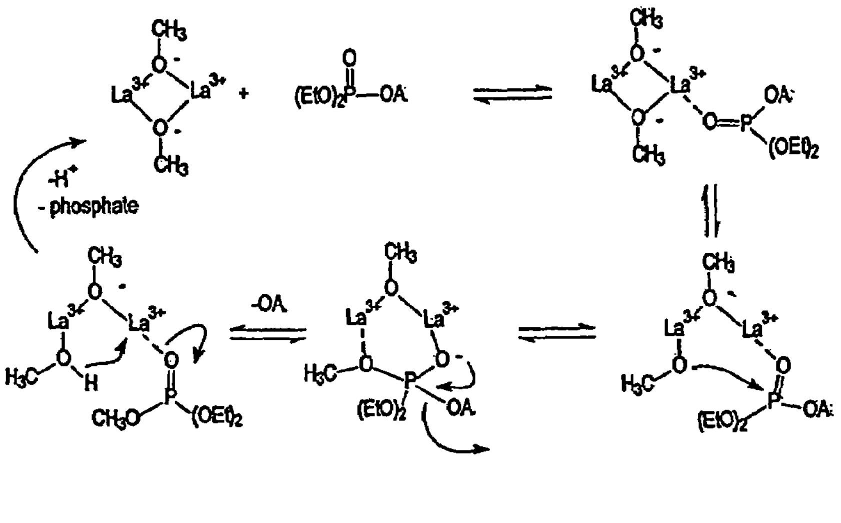
FIG. 1A shows a proposed mechanism for catalysis by a lanthanum methoxide dimer of the methanolysis of an aryl phosphate.

We have shown above that $La^{3+}$ in methanol is a remarkably effective catalyst for the decomposition of paraoxon and that there are three forms of dimeric species which have maximal activities at different ${}_s^s$pH values. Of these, the highest activity is attributed to $La^{3+}{}_2(^-OCH_3)_2$ operating most effectively in the neutral ${}_s^s$pH region between 7.7 and 9.2 (neutral ${}_s^s$pH in methanol is 8.4). Given in FIG. 1A is a proposed mechanism by which $La^{3+}{}_2(^-OCH_3)_2$, as a bis methoxy bridged dimer, promotes the methanolysis of paraoxon. Although none of our $k_{obs}$ vs. [$La^{3+}$] kinetics profiles shows saturation behavior indicative of formation of a strong complex between paraoxon and $La^{3+}$, given the well-known coordinating ability of trialkyl phosphates to lanthanide series metal ions and actinide series metal ions, a first step probably involves transient formation of a {paraoxon:$La^{3+}{}_2$:($^-OCH_3)_2$} complex. Since it is unlikely that the bridged methoxy is sufficiently nucleophilic to attack the coordinated phosphate, in the proposed mechanism, one of the $La^{3+}$—$OCH_3$—$La^{3+}$ bridges opens to reveal a singly coordinated {$La^{3+}$:$^-OCH_3$} adjacent to a Lewis acid coordinated phosphate which then undergoes intramolecular nucleophilic addition followed by ejection of the p-nitrophenoxy leaving group. $La^{3+}{}_2(OCH_3)_2$ is regenerated from the final product by a simple deprotonation of one of the methanols of salvation and dissociation of the phosphate product, $(EtO)_2P(O)OCH_3$.

Example 8

$M^{n+}$-Catalyzed Methanolysis of O,O'-diethyl-S-p-nitrophenylphosphorothioate: Experimental Details, Kinetics and NMR Studies O,O-diethyl-S-p-nitrophenyl phosphorothiolate, when placed in an appropriately buffered methanol solution containing $La^{3+}$ and $^{-}OCH_3$ ions held in the $_s^s$pH region between 7 and 11, underwent rapid methanolysis at ambient temperature to produce diethyl methyl phosphate and 5-mercapto-2-nitrobenzene. A detailed reaction scheme is given in Scheme 2 and reaction conditions are detailed below.

Scheme 2

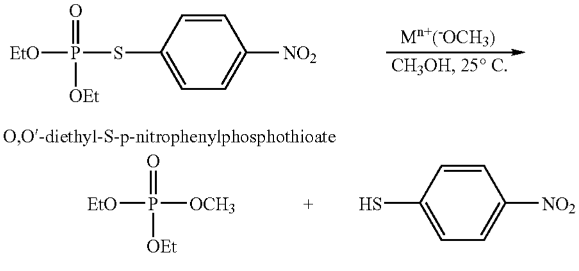

O,O'-diethyl-S-p-nitrophenylphosphothioate

Methyldiethylphosphate

5-Mercapto-2-nitrobenzene

To 4.9 mL of anhydrous methanol at ambient temperature was added N-ethylmorpholine (63.8 μL or 57.7 mg) half neutralized with 11.4 M $HClO_4$ (21.5 μL), so that the final total buffer concentration was 0.1M in 4.95 mL solution. The measured $_s^s$pH of the buffer solution was 8.89. To 0.8 mL of this buffer and 0.2 mL deuterated methanol was added 8.8 mg of O,O-diethyl-S-p-nitrophenyl phosphorothiolate. The $^{31}P$ NMR spectrum of this solution showed a single signal at δ22.39 ppm. Following NMR analysis, a 10 μL aliquot of a lanthanum ion/sodium methoxide/methanol solution was added which had been prepared by dissolving 16.4 mg $La(O_3SCF_3)_3$ in 56.9 μL of 0.5 M sodium methoxide methanol solution. At this point, the concentrations in the NMR tube were: 0.030 M phosphorothiolate, 0.1 M N-ethylmorpholine, 0.01M sodium methoxide and 0.0098 M $La(O_3SCF_3)_3$. The $^{31}P$ NMR spectrum, obtained 103 sec after addition of the aliquot indicated complete disappearance of the phosphorothiolate signal and the appearance of a new signal at δ 3.57 ppm, attributable to diethyl methyl phosphate in the presence of 0.0098 M $La^{3+}$.

The absorbance of a 0.5 mL solution of methanol containing 1 mM of $Cu(OTf)_2$, 1 mM of [12]ane$N_3$, 0.5 mM of $NaOCH_3$ and 0.5 mM of O,O'-diethyl-S-p-nitrophenylphosphorothioate was monitored at 280 nm as a function of time. The reaction exhibited first order kinetics with $k_{obs}$=4.3×$10^{-2}s^{-1}$($t_{1/2}$=16 sec) corresponding to a 8.3×$10^7$-fold acceleration over the background reaction at $_s^s$pH =8.41.

The absorbance of a 2.5 mL solution of methanol containing 1 mM of $Zn(OTf)_2$, 1 mM of [12]ane$N_3$, 0.5 mM of $NaOCH_3$ and 0.5 mM of O,O'-diethyl-S-p-nitrophenylphosphorothioate was monitored at 280 nm as a function of time. The reaction exhibited first order kinetics with $k_{obs}$=4.1×$10^{-4}s^{-1}$($t_{1/2}$=28 min) corresponding to a 4.1×$10^5$-fold acceleration over the background reaction at $_s^s$pH =8.70.

Example 9

$La^{3+}$-Catalyzed Methanolysis of VX: A Prophetic Example

To 200 mL of methanol is added 2.55 mL of N-ethylmorpholine (2.3 g) and 0.86 mL of 11.4 M $HClO_4$ to bring the total buffer concentration to 0.1 M. To this solution is added 1.29 g of $La(O_3SCF_3)_3$ and 4 mL of a 0.5 M solution of $NaOCH_3$ in methanol.

To the above solution is added 2 g of VX (8.33×$10^{-3}$ moles, 0.041 M) and the solution is allowed to stand at ambient temperature for 15 minutes. It is expected that analysis of the resulting solution would indicate substantially complete disappearance of VX.

Example 10

$M^{2+}$-Catalyzed Methanolysis of Fenitrothion

The activity of this system may be increased by adding equimolar amounts of bi- or tri-dentate ligands to complex $Zn^{2+}(^{-}OCH_3)$ and limit oligomerization of $Zn^{2+}(^{-}OCH_3)_2$ in solution. The systems studied herein used methoxide and the ligands phen, diMephen and [12]ane$N_3$. The active forms of the metal ions at neutral $_s^s$pH are $Zn^{2+}(^{-}OCH_3)$ with no added ligand and $\{Zn^{2+}:L:(^{-}OCH_3)\}$ when ligand (L) is present. In the case of phen ligand, decreasing the oligomerization does not prevent the formation $Zn^{2+}(^{-}OCH_3)$ dimers since the bulk of the material is now present as $\{LZn^{2+}(^{-}OCH_3)_2Zn^{2+}L\}$ which is not catalytically active, but is in equilibrium with an active mononuclear form. The propensity to form the latter inactive dimers can be reduced either by increasing the steric interaction (ligand diMephen) or by changing the coordination number (ligand [12]ane$N_3$) in which cases the overall activity of the catalytic system increases. In the case of ligand diMephen, the dimerization is definitely reduced but the binding to the metal ion is not as strong as in the case of phen or [12]ane$N_3$, which means that there is some free $Zn^{2+}$ in solution under the concentrations and $_s^s$pH region where the catalyst is active.

A reaction scheme is given below (Scheme 3) for the methanolysis of fenitrothion where $M^{2+}$ is a transition metal ion, most preferably $Zn^{2+}$ or $Cu^{2+}$. In a preferred embodiment a ligand is present, preferably a bidentate or tridentate ligand, most preferably [12]ane$N_3$ for $Cu^{2+}$ and diMephen or [12]ane$N_3$ for $Zn^{2+}$.

Scheme 3

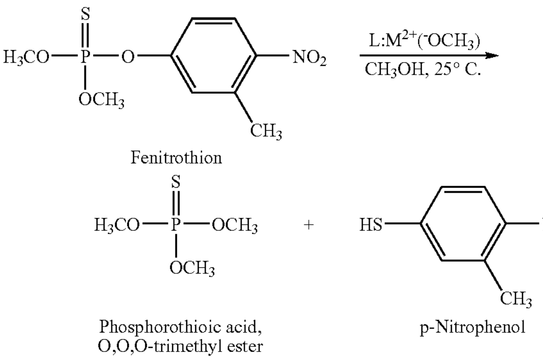

Fenitrothion

Phosphorothioic acid, O,O,O-trimethyl ester p-Nitrophenol

As seen in FIGS. 6 and 7, $Cu^{2+}$:($^{-}OCH_3$) at 25° C. either alone or in the presence of equimolar [12]ane$N_3$, bpy or phen shows both great catalytic efficacy and specificity toward the P═S derivatives.

Apparently matching the hard/soft characteristics of the metal ion and the substrate is important in designing an effective catalytic system for P═S substrates. With due consideration for matching the hard/soft characteristics of the substrate and the metal ion, dramatic rate and selectivity can be achieved in the methanolysis of P═O vs. P═S phosphates.

Example 11

$Zn^{2+}$-Catalyzed Methanolysis of Paraoxon and Fenitrothion

The methanolyses of paraoxon and fenitrothion were investigated as a function of added $Zn(OTf)_2$ or $Zn(ClO_4)_2$ in methanol at 25° C. either alone, or in the presence of equimolar concentration of ligands: phen, diMephen and [12]ane$N_3$. The catalysis requires the presence of methoxide, and when studied as a function of added [$NaOCH_3$], the rate constants ($k_{obs}$) for methanolysis with $Zn^{2+}$ alone or in the presence of equimolar phen or diMephen, maximize at different [$^{-}OCH_3$]/[$Zn^{2+}$]$_{total}$ ratios of 0.3, 0.5 and 1.0 respectively. Plots of $k_{obs}$ vs. [$Zn^{2+}$]$_t$ either alone or in the presence of equimolar ligands phen and diMephen at the [-$OCH_3$]/[$Zn^{2+}$]$_{total}$ ratios corresponding to the rate maxima are curved and show a square root dependence on [$Zn^{2+}$]$_t$. In the cases of phen and diMephen, this is explained as resulting from formation of a non-active dimer, formulated as a bis-μ-methoxide bridged form (L:$Zn^{2+}$($^{-}OCH_3$)$_2$$Zn^{2+}$:L) in equilibrium with an active mononuclear form, L:$Zn^{2+}$($^{-}OCH_3$). In the case of the $Zn^{2+}$:[12]ane$N_3$ system, no dimeric forms are present as can be judged by the strict linearity of the plots of $k_{obs}$ vs. [$Zn^{2+}$]$_t$ in the presence of equimolar [12]ane$N_3$ and $^{-}OCH_3$. Analysis of the potentiometric titration curves for $Zn^{2+}$ alone and in the presence of the ligands allows calculation of the speciation of the various $Zn^{2+}$ forms and shows that the binding to ligands phen and [12]ane$N_3$ is very strong, while the binding to ligand diMephen is weaker. This {$Zn^{2+}$:[12]ane$N_3$:$^{-}$OMe} system exhibits excellent turnover of the methanolysis of paraoxon when the substrate is in excess. A mechanism for the catalyzed reactions is proposed (see FIG. 1B) which involves a dual role for the metal ion as a Lewis acid and source of nucleophilic $Zn^{2+}$-bound $^{-}OCH_3$.

Example 12

$Zn^{2+}$-Catalyzed Methanolysis of Paraoxon and Fenitrothion and p-nitrophenyl acetate A second set of methanolysis experiments was performed with three substrates, namely paraoxon, fenitrothion and p-nitrophenyl acetate, as a function of total added [$Zn(ClO_4)_2$] maintaining the [($^{-}OCH_3$)]/[$Zn^{2+}$]$_{total}$ ratio at 0.3 with added $NaOCH_3$. The three plots shown in FIG. 12 all exhibit a similar curvature independent of the nature of the substrate. The curvature thus cannot be due to substrate binding and is modeled according to the overall process given in equation(5) where an active mononuclear form (assumed to be [$Zn(OCH_3)$]$^+$ is in equilibrium with a non-active dimer. Given in equation (6) is the appropriate kinetic expression based on equation(5) which includes a possible methoxide dependent term ($k_{background}$) which is present for the most reactive substrate (p-nitrophenyl acetate) but not important for the phosphate triesters. This expression shows a square-root dependence on the [$M^{2+}$]$_{total}$. Shown in FIGS. 9A and 9B are the concentration dependencies for the methanolysis of fenitrothion (FIG. 9A) and paraoxon (FIG. 9B) catalyzed by $Zn^{2+}$ alone and in the presence of ligands phen and diMephen where the ratio of [($^{-}OCH_3$)]/[$Zn^{2+}$]$_{total}$ is kept at a constant value (i.e. 0.3 for $Zn^{2+}$ alone, 0.5 for phen, and 1.0 for diMephen).

These plots are also curved, not due to a saturation binding of the phosphorus triesters to the metal, but due to the monomer:dimer equilibrium given in equation(5). The lines through the FIGS. 9A, 9B data are derived on the basis of NLLSQ fits to equation(6) and yield the kinetic constants given in Table 16. As shown in FIG. 13A, the kinetic dependence in the presence of ligand [12]ane$N_3$ is substantially linear and showns no evidence of monomer:dimer equilibrium.

(5)

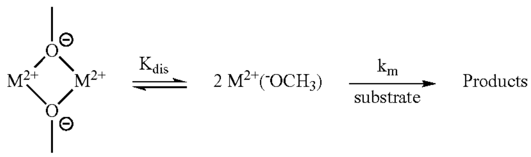

$$k_{obs} = \left\{k_m K_{dis}\left(\sqrt{1 + 8[M^{2+}]_{total} / K_{dis}} - 1\right) \Big/ 4 + k_{background}\right\} \quad (6)$$

Example 13

$Zn^{2+}$-Catalyst Stoichiometry

Potentiometric titration of $Zn(OTf)_2$ solutions of varying concentrations (0.5–2 mM) in anhydrous methanol were performed in the absence and presence of equimolar amounts of ligands phen, diMephen and [12]ane$N_3$ in order to determine the speciation of the $Zn^{2+}$ ions under conditions similar to those of the kinetic experiments.

Independent titrations of 1 mM solutions of each ligand were performed and the resulting data were analyzed using Hyperquad™ 2000 fitting routine providing the $_s^s pK_a$ values for the last acid dissociation step, of 5.63±0.01 for phen-$H^+$, 6.43±0.01 for diMephen-$H^+$ and >13 for [12]ane$N_3$—$H^+$ respectively.

The potentiometric titration curve of $Zn(OTf)_2$ presented in FIG. 14 shows the consumption of two equivalents of methoxide occuring in one rather steep step. In the presence of ligands phen, diMephen and [12]ane$N_3$, the titration curve changes due to the formation of complexes. To analyze these titration data, a number of different dissociation schemes were attempted and the final adopted ones were selected based on goodness of fit to the titration profiles along with due consideration of the various species suggested by the kinetic studies.

The case of the ligand triazacrown ether [12]ane$N_3$ is the simplest to analyze since we have no evidence supporting the presence of any species containing more than one $Zn^{2+}$ ion. This fact, coupled with the high $_s^s pK_2$ of [12]ane$N_3$—$H^+$, allows one to define the relevant species in solution as [12]ane$N_3$—$H^+$, $Zn^{2+}$:[12]ane$N_3$, $Zn^{2+}$:[12]ane$N_3$:($^{-}OCH_3$)

and $Zn^{2+}$:[12]ane$N_3$:($^-OCH_3$)$_2$, which, when fit via the Hyperquad™ 2000 program, produces a theoretical titration curve (FIG. 14) which is in excellent agreement with the observed curve. The best fit formation constants for [12]ane$N_3$—$H^+$, $Zn^{2+}$:[12]ane$N_3$, $Zn^{2+}$:[12]ane$N_3$:($^-OCH_3$) and $Zn^{2+}$:[12]ane$N_3$:2($^-OCH_3$) are given in Table 15. The $Zn^{2+}$ speciation diagram constructed from these constants (not shown) indicates that in the $_s^s$pH region used in our kinetic studies, greater than 95% of the total $Zn^{2+}$ is present as $Zn^{2+}$:[12]ane$N_3$:($^-OCH_3$). Shown in FIG. 13A is a plot of the pseudo-first order rate constants for the methanolysis of paraoxon in the presence of Zn(OTf)$_2$with a right hand axis depicting the [$Zn^{2+}$:[12]ane$N_3$:($^-OCH_3$)] as function of total [Zn(OTf)$_2$]. The very good correlations between the kinetic data and the speciation data strongly supports $Zn^{2+}$:[12]ane$N_3$:($^-OCH_3$) as the catalytically active component, with a derived second order rate constant of 50.4 $M^{-1}$ $min^{-1}$ for the methanolysis of paraoxon.

Potentiometric titration of an equimolar mixture of Zn(OTf)$_2$ and phen in the presence of 0.6 equivalents of perchloric acid showed that all the added $H^+$ was released in the strong acid region below $_s^s$pH 3 with one additional step consuming a single equivalent of methoxide around $_s^s$pH 10. The former indicates strong binding between $Zn^{2+}$ and phen even at $_s^s$pH=3, but does not allow us to determine an exact value of the $Zn^{2+}$: phen binding constant other than to set a lower limit for its formation constant of $10^{10}$ $M^{-1}$ which was used as a fixed value in all subsequent fittings. In the higher $_s^s$pH region where the kinetic experiments were performed, we employed a model where the $Zn^{2+}$ exists predominantly as {$Zn^{2+}$: phen:($^-OCH_3$)}$_2$ and $Zn^{2+}$: phen:($^-OCH_3$)$_2$, both of these being inferred by the kinetic data. Hyperquad™ 2000 fitting of the full titration profile using the previously determined stability constants for phen-$H^+$ and $Zn^{2+}$:phen, produces a good fit and provides respective stability constants for {$Zn^{2+}$: phen:($^-OCH_3$)}$_2$ and $Zn^{2+}$: phen:($^-OCH_3$)$_2$ given in Table 15.

In the catalysis of methanolysis of paraoxon and fenitrothion by {$Zn^{2+}$:$^-$OMe}, either alone or in the presence of complexing ligands,two things are clear: first, $Zn^{2+}$ species are appreciably soluble in solution at all $_s^s$pH values and all concentrations employed; and second, equilibria consisting of dimeric species in equilibrium with a kinetically active mononuclear species are formed in the case of $Zn^{2+}$, {$Zn^{2+}$: phen} and {$Zn^{2+}$:diMephen}, but not in the case of {$Zn^{2+}$: [12]ane$N_3$} where only the kinetically active mononuclear form is present. High solubility of $Zn^{2+}$ has been found with triflate and perchlorate counterions. These anions are preferred for their relative kinetic inertness since they give the highest rates for catalyzed reactions relative to other anions such as bromide, chloride or acetate. Methanolysis of paraoxon, catalyzed by 1 mM Zn(OTf)$_2$ with 0.3 equation of added $NaOCH_3$ is relatively unaffected by the addition of up to 5 mM NaOTf or $NaClO_4$, but is significantly inhibited by the addition of 1 mM NaCl, NaBr or Na($O_2CCH_3$).

The ability of the $Zn^{2+}$ species to methanolyze both the P═O and P═S species with second-order rate constants 50-to 1000-fold larger than the corresponding second-order rate constants for methoxide attack alone may be due to the bifunctional nature of the catalyst and partly due to the reduced dielectric constant of the medium and its reduced solvation of metal ions relative to water.

Preparatively useful forms of catalysts can be generated by the addition of known amounts of ligand, Zn(OTf)$_2$ and methoxide. In the case of a solution comprising 2 mM Zn(OTf$_2$, 2 mM diMephen ligand and 2 mM $NaOCH_3$ which generates a $_s^s$pH of ~9.5, methanolysis of paraoxon is accelerated 1.8×$10^6$-fold and methanolysis of fenitrothion is accelerated 13×$10^6$-fold. Likewise, a solution comprising 1 mM of Zn(OTf)$_2$, 1 mM [12]ane$N_3$ ligand and 0.5 mM $NaOCH_3$ generates a $_s^s$pH of 9.3 and methanolysis of paraoxon is accelerated 1.7×$10^6$-fold.

Unlike the dimeric form of $La^{3+}$, which are effective for methanolyzing paraoxon, dimeric forms of $Zn^{2+}$ are not as effective as its monomers.

Example 14

$Zn^{2+}$-Catalyzed Methanolysis of Paraoxon and Fenitrothion: Kinetic and Potentiometric Studies The kinetics for $Zn^{2+}$-catalyzed methanolysis of paraoxon and fenitrothion fall into two distinct classes depending on what ligand is coordinated to the metal ion and how much methoxide is added. Without any ligand, as shown in FIG. 11, the $k_{obs}$ for methanolysis of paraoxon in the presence of 1 mM Zn(OTf)$_2$ is maximized between 0.1 and 0.4 mM added $NaOCH_3$. There is an initially very strong dependence on the concentration of methoxide, the slope of which for the first 0.05 equationadded yields a second order rate constant of ~34 $M^{-1}$ $min^{-1}$ for methanolysis of paraoxon. Undoubtedly this methoxide is coordinated to $Zn^{2+}$ to establish the $\{Zn(OCH_3)\}_2^{2+} \rightleftharpoons 2\ \{Zn(OCH_3)\}^+$ equilibrium but as additional methoxide is added, the overall rate drops significantly suggesting formation of inactive species having a [($^-OCH_3$)]/[$Zn^{2+}$] greater than 1. This agrees with a potentiometric titration of $Zn^{2+}$ in methanol which displayed a steeper-than-normal consumption of 2 methoxides in an apparent single event having a midpoint of ~$_s^s$p$K_a$ 9.8 which, when analyzed via Hyperquad™ fitting to a model containing only the mononuclear species $Zn^{2+}$($OCH_3^-$) and $Zn^{2+}$($OCH_3^-$)$_2$, gives apparent $_s^s$p$K_{a^1}$ and $_s^s$p$K_{a^2}$ values of 10.66 and 8.94. While our original fitting (Gibson, et al., 2003) did not include dimer and oligomer formation, the fact that the second apparent $_s^s$p$K_a$ is lower than the first indicates some cooperative effect facilitating addition of a second methoxide per $Zn^{2+}$ ion before the first addition is stoichiometrically complete. This fact limits the amount of any forms having a methoxide/$Zn^{2+}$ stoichiometry of 1 and shifts the maximum of the kinetic plot in FIG. 11 to the left. Species where the methoxide/$Zn^{2+}$ ratio>1 probably exist in solution as oligomers of $\{Zn^{2+}(^-OCH_3)_{1.5\text{-}2}\}_n$ held together with methoxide bridges. Added bi- or tridentate ligands could, in principle, disrupt this arrangement by capping one face of the Zn favouring the formation of dimers and monomers of stoichiometry {$Zn^{2+}$:L($^-OCH_3$)}$_2$, $Zn^{2+}$:L($^-OCH_3$)($HOCH_3$) or $Zn^{2+}$:L($^-OCH_3$)$_2$ depending on the methoxide/$Zn^{2+}$ ratio. Indeed, as shown in FIG. 8, ligands phen, diMephen and [12]ane$N_3$ modify the kinetic behaviour in important ways depending on whether the methoxide/$Zn^{2+}$ ratio is less than or greater than 1.

Example 15

$Zn^{2+}$-Catalyzed Methanolysis of Paraoxon: NMR Studies of Catalytic Turnover A $^{31}P$ NMR experiment was performed to determine a turnover rate for the methanolysis of paraoxon using $Zn^{2+}$: diMephen:$^-OCH_3$.

To 0.6 mL of dry methanol (with 20% of $CD_3OD$ as an NMR lock signal) containing 1 mM each of Zn(OTf)$_2$, diMephen and $NaOCH_3$ at ambient temperature was added 2.54 mg of paraoxon. At this point the concentration of paraoxon was 15 mM and that of $Zn^{2+}$: diMephen: $^{-}OCH_3$ was taken as 1.0 mM with the measured $_s^spH$ of the methanol solution being 8.75, close to neutrality (8.34). The $^{31}P$ NMR spectrum of the solution was monitored periodically over ~160 minutes at which time it indicated complete disappearance of the paraoxon signal which had been at δ-6.35 ppm and complete appearance of a new signal at δ 0.733 ppm corresponding to the product diethyl methyl phosphate. The $^1H$ NMR spectrum was obtained after 150 min and it confirmed the complete disappearance of the starting material and full release of the product p-nitrophenol.

The $^{31}P$ NMR spectrum of a solution containing 15 mM paraoxon and 1 mM in each of $Zn(OTf)_2$, $NaOCH_3$ and ligand diMephen was continuously monitored at ambient temperature over a period of ~160 minutes. The spectra were summed each 15 minutes to produce the time profile given in FIG. 10 which displays the disappearance of paraoxon and the appearance of a new signal at δ 0.733 ppm attributed to diethyl methyl phosphate. Fitting of these two time profiles to a first order expression gave an average pseudo-first order rate constant of $(4.5\pm0.1)\times10^{-4}\ s^{-1}$ over 15 turnovers ($t_{1/2}$=25 min), thus showing the true catalytic nature of the system.

Example 16

$Zn^{2+}$-Catalyzed Methanolysis of Paraoxon and Fenitrothion: Kinetics

As shown by the various formation constants given in Table 15, phen binds very tightly to $Zn^{2+}$ at all values in methanol. According to potentiometric titration data, the major species in the $_s^spH$ domain surrounding 0<[methoxide]/$[Zn^{2+}]_t$<1 is the dimer $\{Zn^{2+}:phen:(^{-}OCH_3)\}_2$ which is in equilibrium with a small amount of kinetically active monomer, $\{Zn^{2+}phen(^{-}OCH_3)\}$. Under conditions where the [methoxide]/$[Zn^{2+}]_t$=0.5, a plot of $k_{obs}$ for catalyzed methanolysis of paraoxon vs. $[Zn^{2+}]_{total}$ (see FIG. 14B) follows the square root dependence of equation (6) that corresponds to the process presented in equation (5) with the derived kinetic parameters being given in Table 16. The same general phenomenon is seen with ligand diMephen although its binding to $Zn^{2+}$ is weaker than phen (as is known to be the case in water) such that at any given $_s^spH$, only about 85% of the $Zn^{2+}$ is bound to diMephen.

TABLE 15

Formation constants for various species determined by potentiometric titration.

| Equilibrium | Log $_s^sK$ L = phen | Log $_s^sK$ L = diMephen | Log $_s^sK$ L = [12]ane$N_3$ |
|---|---|---|---|
| $[L-H^+]/[L][H^+]$ | 5.63 | 6.43 | 14.92 |
| [ZnL]/[L][Zn] | 10 | 4.25 | 10.11 |
| $[Zn_2L_2(OMe)_2]/[L]^2[Zn]^2[OMe]^2$ | 36.33 | 28.05 | |
| $[ZnL(OMe)_2]/[L][Zn^{2+}][OMe]^2$ | 20.58 | | 21.67 |
| [ZnL(OMe)]/[L][Zn][OMe] | | | 17.79 |

TABLE 16

Kinetic constants for the methanolysis of fenitrothion and paraoxon catalyzed by $Zn^{2+}$ in the absence and presence of ligands phen, diMephen, [12]ane$N_3$, at T = 25° C.

| Catalyst | $K_{dis}$ (mM)[a] | Paraoxon $k_m$ ($M^{-1}min^{-1}$)[a] | Fenitrothion $k_m$ ($M^{-1}min^{-1}$)[a] |
|---|---|---|---|
| $^{-}OCH_3$ | — | 0.66 | 0.043 ± 0.001 |
| $Zn^{2+}$[b] | <0.005 | 72.5 ± 1.5 | 11.2 ± 0.4 |
| $\{Zn^{2+}$:phen$\}$[c] | <0.005 | 124 ± 2.5 | 19.0 ± 0.6 |
| $\{Zn^{2+}:phen:2(^{-}OCH_3)\}$[d] | — | 29.5 ± 0.7 | 2.7 ± 0.1 |
| $Zn^{2+}$:diMephen[e] | 0.6 ± 0.2 | 101 ± 1 | 48.0 ± 0.7 |
| $Zn^{2+}:[12]aneN_3:(^{-}OCH_3)$[f] | — | 50.8 ± 0.8 | 2.9 ± 0.1 |
| $\{2La^{3+}:2(^{-}OCH_3)\}$[g] | — | 2830 ± 140 | No catalysis |

[a]Dimer dissociation constant ($K_{dis}$) and conditional second order rate constant ($k_m$) for monomer defined as in equation(5); "—" means non-applicable since there is no observable dimerization under the specific conditions.
[b]Based on NLLSQ fits of $k_{obs}$ vs. $[Zn^{2+}]_{total}$ data to equation(6) at [methoxide]/$[Zn^{2+}]_{total}$ ratio of 0.3
[c]Based on NLLSQ fits of $K_{obs}$ vs. $[Zn^{2+}:phen]_{total}$ data to equation(6) at [methoxide]/$[Zn^{2+}]_t$ ratio of 0.5
[d]Based on linear fits of $K_{obs}$ vs. $[Zn^{2+}:phen]_{total}$ data to equation(6) at [methoxide]/$[Zn^{2+}]_t$ ratio of 2.0
[e]Based on NLLSQ fits of $K_{obs}$ vs. $[Zn^{2+}:diMephen]_{total}$ data to equation(6) at [methoxide]/$[Zn^{2+}]_{total}$ ratio of 1.0
[f]Based on linear fits of $K_{obs}$ vs. $[Zn^{2+}:[12]aneN_3:(^{-}OCH_3)]_t$ data at [methoxide] = $[Zn^{2+}]_{total}$ = [[12]ane$N_3$].
[g]From reference Tsang et al., 2003

Figure 1B:
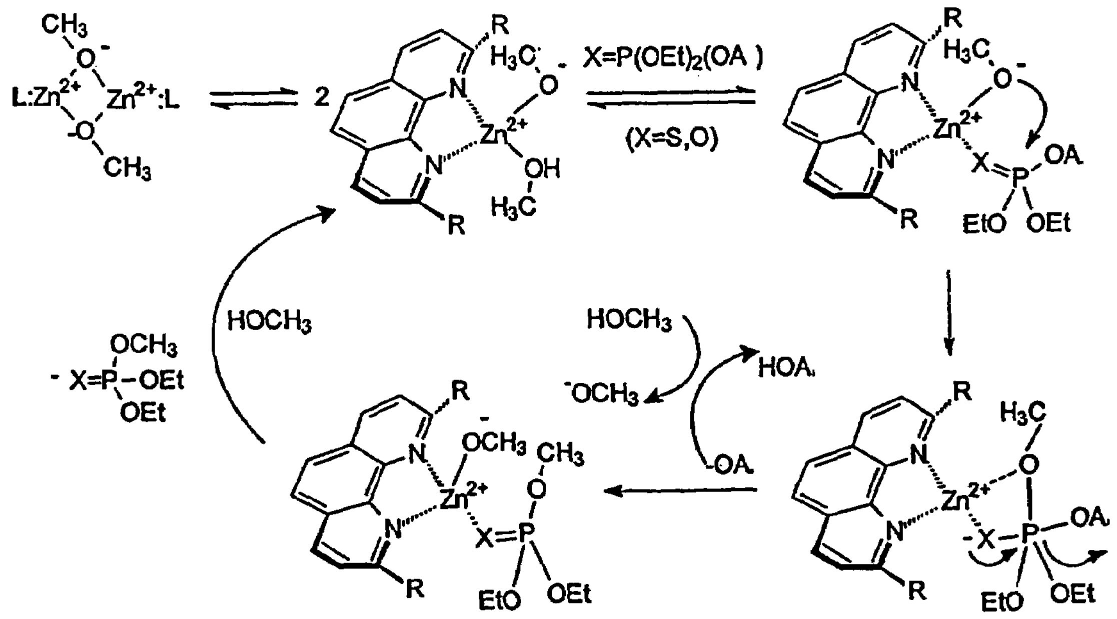
FIG. 1B shows a proposed mechanism for catalysis by a zinc methoxide complex of the methanolysis of an aryl phosphate.
Figure 1C:
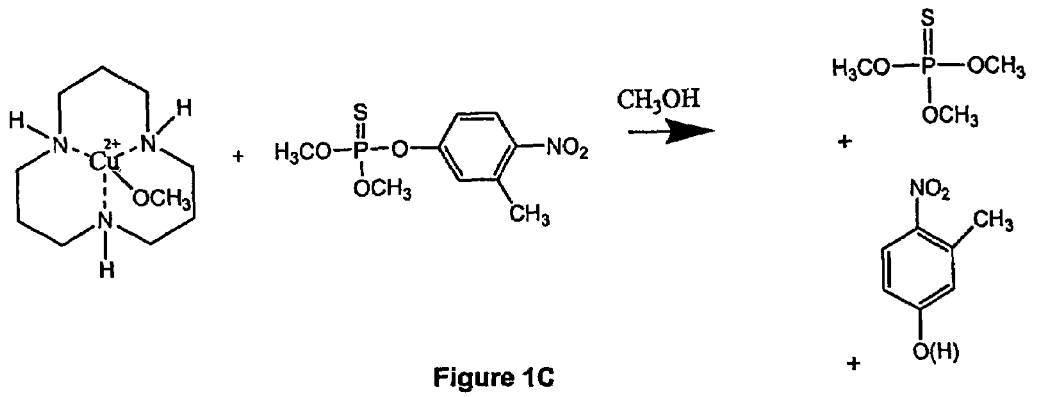
FIG. 1C shows the reaction scheme for Cu:[12]ane$N_3$ catalyzing the methanolysis of fenitrothion.

As shown in FIG. 8 for the methanolysis of paraoxon, the $Zn^{2+}$:phen and $Zn^{2+}$:diMephen systems behave differently in the 1<[methoxide]/$[Zn^{2+}]_{total}$<2 domains with the overall activity increasing and decreasing respecively. Because of the weak binding inherent in the $Zn^{2+}$:diMephen system, the additional methoxide probably displaces the ligand from the $\{Zn^{2+}:diMephen:(^{-}OCH_3)\}_{1,2}$, forms to generate uncomplexed diMephen and $\{Zn(OCH_3)_2\}_n$ oligomers which are not active. However, because of the far stronger binding of phen to $Zn^{2+}$, the additional methoxide breaks apart the $\{Zn^{2+}:phen:(^{-}OCH_3)\}_2$ dimer as shown in FIG. 1B to form $Zn^{2+}:phen:(^{-}OCH_3)_2$. The presence of $Zn^{2+}:phen:(^{-}OCH_3)_2$ and its catalytic viability is respectively confirmed by the potentiometric titration data and by the fact that a plot of $k_{obs}$ for methanolysis of both substrates vs. $[Zn^{2+}]_t$ under conditions where the $[Zn^{2+}]$:phen:methoxide ratio is 1:1:2 gives a straight line with a slope of $k_m=29.5\ M^{-1}\ min^{-1}$ for the methanolysis of paraoxon and $k_m=2.7\ M^{-1}s^{-1}$ for the methanolysis of fenitrothion.

The $Zn^{2+}:[12]aneN_3:^{-}OCH_3^{-}$ system is a simple one because of very strong binding and the lack of formation dimers $\{Zn^{2+}:[12]aneN_3:(^{-}OCH_3)\}_2$ under employed conditions. In methanol, the $M^{2+}$-L binding constant is large (log $_s^sK$=10.1 1), ensuring that there is essentially no free ligand in solution, and the $_s^spK_a$ for ionization of the complex $Zn^{2+}:[12]aneN_3:HOCH_3$ is 9.1. The $k_{obs}$ vs. $[Zn^{2+}]_{total}$ plot shown in FIG. 13A is a straight line consistent with $(Zn^{2+}:[12]aneN_3:(^{-}OCH_3))$ being the active catalyst and predominant form.

Example 17

$Cu^{2+}$-Catalyzed Methanolysis of Paraoxon and Fenitrothion: Kinetic Studies In the absence of metal ions, uncatalyzed attack of methoxide on paraoxon is some 15 times faster than on fenitrothion, but in the presence of all $\{Cu^{2+}: (^{-}OCH_3)\}$ species are more effective for fenitrothion than paraoxon. This can be quantified by the relative selectivity parameter given in Table 18 which compares the relative reactivity of the metal-coordinated methoxide reaction relative to free methoxide attack for P═S and P═O substrates. Relative Selectivity parameters clearly correlate with the hard/soft properties of the metal ion. The "hard" ion $La^{3+}$ exhibits exclusive selectivity for the P═O substrate (relative selectivity parameter ~0), while the softer $Zn^{2+}$ ion shows almost equal affinity for P═O and P═S substrates (relative selectivity parameter ~1). Of the three ions, $Cu^{2+}$ is softest, and exhibits very high selectivities for the P═S substrates with relative selectivity parameter values from ~55–340 with the highest values exhibited in the case of the aromatic ligands. The best combination of selectivity and overall high catalytic activity is achieved with {[12]ane$N_3$:$Cu^{2+}$:($^-OCH_3$)} perhaps due to reduced dimerization. All the $Cu^{2+}$-catalyzed reactions proceed with computed second order rate constants larger than those for the uncatalyzed attack of methoxide on paraoxon or fenitrothion which indicates that there is a dual role for the metal ion. As in other $M^{n+}$-promoted hydrolytic and methanolytic reactions, the metal ion is reasonably proposed to deliver a $M^{n+}$-coordinated $OH^-$ or $CH_3O^-$ and act as a Lewis acid to polarize a P═S or P═O unit, which provides both rate and selectivity enhancement. There is a 17,000-fold enhancement of attack of [12]ane$N_3$:$Cu^{2+}$:($^-OCH_3$) on fenitrothion vs. attack of free $^-OCH_3$ even though the latter is ~$10^8$-fold more basic. This represents the largest acceleration reported for metal-catalyzed phosphoryl transfer reactions to solvent. Through turnover experiments, it has been demonstrated that this is a truly catalytic system which, at millimolar concentration can provide $1.7\times10^9$-fold acceleration of the methanolysis of fenitrothion at neutral $_s^s$pH and ambient temperature.

In the presence of ligand [12]ane$N_3$, the kinetic plots, $k_{obs}$ vs. $[Cu(OTf)_2]_{total}$ (see FIG. 7), for methanolysis of paraoxon and methanolysis of fenitrothion are strictly linear which is indicative of complete formation of a mononuclear catalyst of the structure: [12]ane$N_3$:$Cu^{2+}$:($^-OCH_3$). The second order rate constants, $k_m$, for paraoxon and for fenitrothion were evaluated as the gradients of the linear plots, these values being given in Table 18.

The kinetics of methanolysis were monitored at 25° C. in anhydrous methanol by observing the rate of appearance of p-nitrophenol or 3-methyl4-nitrophenol between 312 and 335 nm at [paraoxon] or [fenitrothion]=4 to $12\times10^{-5}$ M under pseudo-first order conditions of excess $Cu(OTf)_2$ (0.2 to $5.0\times10^{-3}$ M). All reactions were followed to at least three half times and found to exhibit good pseudo-first order rate behavior and the first order rate constants ($k_{obs}$) were evaluated by fitting the Abs. vs. time traces to a standard exponential model. The kinetics were all determined under self-buffered conditions where the $_s^s$pH was controlled by a constant $Cu^{2+}$/$Cu^{2+}$($^-OCH_3$) ratio and in the cases with ligands [12]ane$N_3$, bpy and phen, these were added in amounts equivalent to the $[Cu^{2+}]_{total}$. Under these conditions the observed $_s^s$pH values correspond to the apparent $_s^spK_a$ value for ionization of the {$Cu^{2+}$:L:($HOCH_3$)} ⇌ {$Cu^{2+}$:L:($^-OCH_3$)}+$^+H_2OCH_3$ system.

As shown in FIGS. 6 and 7 the overall behaviour portrayed in the $k_{obs}$ vs. [$Cu^{2+}$] plots falls into two categories depending on the nature of the ligand employed. In the absence of any ligand, or in the presence of equimolar bpy or phen, the FIG. 6 plots are non-linear and indicative of a square-root dependence which can be fit via a standard Non-Linear Least Squares (NLLSQ) treatment to equation (6) derived on the following assumptions: all the ligand is bound to $Cu^{2+}$; an active (rate constant $k_m$) mononuclear species {$Cu^{2+}$:L:($^-OCH_3$)} is in rapid equilibrium (dissociation constant $K_{dis}$) with an inactive dimer (equation 4) and $k_{background}$ is negligible since it is undetectable. How good the fit of the lines is may be seen by examining the computed lines through the FIG. 6 data and the best fit constants are given in Table 18. Also in Table 18 are the measured $_s^s$pH values over the entire [$Cu^{2+}$] range under the self-buffering conditions which deviate by an acceptable 0.2 or less units. In the case of paraoxon, the catalyzed reactions were sufficiently slow that we have placed upper limits on the rate and equilibrium constants.

A system comprising 2 mM $Cu(OTf)_2$, along with 0.5 equation of $N(Bu)_4OCH_3$ and 1 equivalent of [12]ane$N_3$ catalyzes the methanolysis of fenitrothion with a $t_{1/2}$ of ~58

TABLE 18

Kinetic constants for thte methanolysis of paraoxon and fenitrothion catalyzed by $Cu^{2+}$ in the absence and presence of ligands [12]ane$N_3$, bpy and phen at T = 25° C.

| Catalyst | $_s^s$pH at 0.5 eq of base | $K_{dis}$ (mM)[a] | Paraoxon $k_m$ ($M^{-1}s^{-1}$)[a] | Fenitrothion $k_m$ ($M^{-1}s^{-1}$)[a] | Relative selectivity[b] |
|---|---|---|---|---|---|
| $^-OCH_3$ | | N.A | $1.1\times10^{-2}$ | $(7.2 \pm 0.2)\times10^{-4}$ | 1 |
| $Cu^{2+}$:($^-OCH_3$)[c] | 6.86 ± 0.2 | <0.005 | 0.22 ± 0.02 | 0.79 ± 0.03 | 55 |
| $Cu^{2+}$:bpy:($^-OCH_3$)[d] | 7.8 ± 0.2 | <0.005 | <0.2 | 4.48 ± 0.12 | 342 |
| $Cu^{2+}$:phen:($^-OCH_3$)[e] | 7.45 ± 0.2 | <0.005 | <0.2 | 2.44 ± 0.06 | 186 |
| $Cu^{2+}$:[12]ane$N_3$:($^-OCH_3$)[f] | 8.75 ± 0.1 | — | 2.76 ± 0.17 | 12.2 ± 0.4 | 67 |
| $Zn^{2+}$:[12]ane$N_3$:($^-OCH_3$)[g] | 9.3 | — | 0.85 ± 0.01 | $(4.8 \pm 0.2)\times10^{-2}$ | 0.86 |
| $La^{3+}{}_2$($^-OCH_3$)$_2$[h] | | — | 47.2 ± 2.3 | No catalysis | ~0 |

[a]Dimer dissociation constant ($K_{dis}$) and conditional second order rate constant ($k_m$) for reaction with monomer defined as in text. "–" means non-applicable since there is no observable dimerization under the specific conditions. The $K_{dis}$ of <0.005 indicates very strong dimerization and is quoted as an upper limit based on an iterative fitting procedure which provided the lowest standard deviations.
[b]Defined as $(k_m/(k_{OCH3})^{fenitrothion}/(k_m/(k_{OCH3})^{paraoxon}$
[c]Based on NLLSQ fits of $k_{obs}$ vs. $[Cu^{2+}]_{total}$ data to equation(6) at [methoxide]/$[Cu^{2+}]_{total}$ ratio of 0.5
[d]Based on NLLSQ fits of $k_{obs}$ vs. $[bpy:Cu^{2+}]_{total}$ data to equation(6) at [methoxide]/$[Cu^{2+}]_{total\ ratio\ of}$ 0.5
[e]Based on NLLSQ fits of $k_{obs}$ vs. $[phen:Cu^{2+}]_{total}$ data to equation(6) at [methoxide]/$[Cu^{2+}]_{t\ ratio\ of\ 0.5}$
[f]Based on linear fits of $k_{obs}$ vs. $[Cu^{2+}:[12]aneN_3:[^-OCH_3)]_{total}$ data at methoxide]/$[Cu^{2+}]_t$ratio of 0.5.
[g]From reference Desloges, et al. 2004.
[h]From reference Tsang et al., 2003.

sec accounting for a $1.7\times10^9$-fold acceleration of the reaction relative to the background reaction at a near neutral $_s^s$pH of 8.75. In this system the concentration of catalyst is in excess over the concentration of fentrothion.

A turnover experiment with substrate in excess of catalyst was conducted using 0.4 mM $Cu(OTf)_2$ along with equimolar [12]ane$N_3$ and 0.5 equationof $NBu_4OCH_3$. The methanolysis of 2 mM fenitrothion was monitored by UV/vis at T=25.0° C. and showed 10 turnovers relative to the active catalyst (0.2 mM $Cu^{2+}$:[12]ane$N_3^-$:($^-OCH_3$)) within 100 min.

Although this invention is described in detail with reference to preferred embodiments thereof, these embodiments are offered to illustrate but not to limit the invention. It is possible to make other embodiments that employ the principles of the invention and that fall within its spirit and scope as defined by the claims appended hereto.

References

Bosch, E.; Rived, F.; Roses, M.; Sales, J., "Hammett-Taft and Drago Models in the Prediction of Acidity Constant Values of Neutral and Cationic Acids in Methanol" *J. Chem. Soc., Perkin Trans.* 2, 1999, 1953.

Bosch, E.; Bou, P.; Allemann, H.; Rosés, M. "Retention of Ionizable Compounds on HPLC. pH Scale in Methanol-Water and the pK and pH Values of Buffers" *Anal. Chem.* 1996, 3651

Brown, R. S.; Neverov, A. A., "Acyl and Phosphoryl Transfer to Methanol Promoted by Metal Ions" *J. Chem. Soc. Perkin* 2 2002, 1039.

Brown, R. S.; Zamkanei, M., "Hydrolysis of Neutral Phosphate and Phosphonate Esters Catalysed by $Co^{2+}$-Chelates of Tris-Imidazolyl Phosphines" *Inorg. Chim. Acta.* 1985, 108, 201.

Desloges, W.; Neverov, A. A.; Brown, R. S., "$Zinc^{2+}$-Catalyzed Methanolysis of Phosphate Triesters: a Process for Catalytic Degradation of the Organophosphorus Pesticides Paraoxon and Fenitrothion" *Inorg. Chem.* 2004, submitted.

Gans, P.; Sabatini, A.; Vacca, A., "Investigation of Equilibria in Solution. Determination of Equilibrium Constants with the HYPERQUAD Suite of Programs" *Talanta.* 1996 43, 1739.

Gibson, G.; Neverov, A. A.; Brown, R. S., "Potentiometric Titration of Metal Ions in Methanol" *Can. J. Chem.* 2003, 81, 495.

Neverov, A. A.; Brown, R. S., "Catalysis of the Methanolysis of Acetylimidazole by Lanthanum Triflate" *Can. J. Chem.* 2000, 78, 1247.

Neverov, A. A.; Brown, R. S., "$La^{3+}$-Catalyzed Methanolysis of Phosphate Diesters. Remarkable Rate Acceleration of the Methanolysis of Diphenyl Phosphate, Methyl p-Nitrophenyl Phosphate, and Bis(p-nitrophenyl) Phosphate" *Inorg. Chem.* 2001(a), 40, 3588.

Neverov, A. A.; McDonald, T.; Gibson, G.; Brown, R. S., "Catalysis of Transesterification Reactions by Lanthanides—Unprecedented Acceleration of Methanolysis of Aryl and Alkyl Esters Promoted by $La(OTf)_3$ at Neutral $_s^s$pH and Ambient Temperatures" *Can. J. Chem.* 2001(b), 79, 1704.

Neverov, A. A.; Montoya-Pelaez, P. J.; Brown, R. S., "Catalysis of the Methanolysis of Activated Amides by Divalent and Trivalent Metal Ions. The Effect of $Zn^{2+}$, $Co^{2+}$, and $La^{3+}$ on the Methanolysis of Acetylmidazole and Its $(NH_3)_5Co^{III}$ Complex" *J. Am. Chem. Soc.* 2001(c), 123, 210.

Rived, F.; Rosés, M.; Bosch, E., "Dissociation Constants of Neutral and Charged Acids in Methyl Alcohol. The Acid Strength Resolution" *Anal. Chim. Acta* 1998, 374, 309.

Tsang, J.; Neverov, A. A.; Brown, R. S., "Billion-Fold Acceleration of the Methanolysis of Paraoxon Promoted by $La(OTf)_3$ in Methanol" *J. Am. Chem. Soc.* 2003, 125, 7602.

Yang, Y.-C.; Berg, F. J.; Szafraniec, L. L.; Beaudry, W. T.; Bunton, C. A.; Kumar, A., "Peroxyhydrolysis of Nerve Agent VX and Model Compounds and Related Nucleophilic Reactions" *J. Chem. Soc. Perkin Trans.* 2 1997, 607.

Yang, Y.-C., "Chemical Detoxification of Nerve Agent VX" *Acc. Chem. Res.* 1999, 32, 109–115.

We claim:

1. A method for decomposing a neutral organophosphorus compound, comprising:

subjecting said neutral organophosphorus compound to an alcoholysis reaction in a substantially non-aqueous medium comprising non-radioactive metal ions selected from the group consisting of lanthanide series metal ions, transition metal ions, and combinations thereof, and alkoxide ions;

wherein said alkoxide ions are present in a range from a trace amount to a metal ion:alkoxide ion ratio of 1:2; and wherein, through said alcoholysis reaction, said neutral organophosphorus compound is decomposed.

2. The method of claim 1, wherein said organophosphorus compound has the following formula (10):

(10)

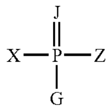

where:

J is O or S;

X, G, Z are the same or different and are selected from the group consisting of Q,OQ, QA, OA, F, Cl, Br, I, QS, SQ, SA and C≡N, wherein at least one of X, G, Z is not Q or QA;

Q is a substituted or unsubstituted branched, straight-chain or cyclic alkyl group having 1–100 carbon atoms; and A is a substituted or unsubstituted moiety selected from the group consisting of phenyl, biphenyl, benzyl, pyridyl, naphthyl, polynuclear aromatic, and aromatic and non-aromatic heterocyclic; and wherein said substituents are selected from the group consisting of Cl, Br, I, F, nitro, nitroso, Q, alkenyl, OQ, carboxyalkyl, acyl, $SO_3H$, $SO_3Q$, S═O(Q), S(═O)$_2$Q, amino, alkylamino (NHQ), arylamino (NHA), alkylarylamino, dialkylamino and diarylamino.

3. The method of claim 1, wherein said medium is a solution further comprising a solvent selected from the group consisting of methanol, substituted and unsubstituted primary, secondary and tertiary alcohols, alkoxyalkanol, aminoalkanol, and combinations thereof.

4. The method of claim 1, wherein said organophosphorus compound has at least one phosphorus atom double bonded to an oxygen or a sulfur atom.

5. The method of claim 1, wherein said medium further comprises a non-inhibitory buffering agent.

6. The method of claim 5, wherein said buffering agent is selected from the group consisting of anilines, N-alkylanilines, N,N-dialkylanilines, N-alkylmorpholines, N-alkylimidazoles, 2,6-dialkylpyridines, primary, secondary and tertiary amines, trialkylamines, and combinations thereof.

7. The method of claim 1, wherein said medium is a solution further comprising a solvent selected from the group consisting of methanol, ethanol, n-propanol, isopropanol, n-butanol, 2-butanol, methoxyethanol, and combinations thereof.

8. The method of claim 7, wherein said solution further comprises a solvent selected from the group consisting of nitriles, esters, ketones, amines, ethers, hydrocarbons, substituted hydrocarbons, unsubstituted hydrocarbons, chlorinated hydrocarbons, and combinations thereof.

9. The method of claim 1, wherein the metal ion:alkoxide ion ratio is in a range from 1:0.01 to 1:2.

10. The method of claim 1, wherein the metal ion: alkoxide ion ratio is in a range from 1:0.1 to 1:2.

11. The method of claim 1, wherein the metal ion:alkoxide ion ratio is in a range from 1:1 to 1:1.5.

12. The method of claim 1, wherein said medium is prepared by combining a metal salt and an alkoxide salt with at least one of alcohol, alkocyalkanol and aminoalkanol.

13. The method of claim 1, wherein said metal ions are selected from the group consisting of lanthanide series metal ions, copper, platinum, palladium, zinc, nickel, yttrium, scandium ions, and combinations thereof.

14. The method of claim 1, wherein said metal ions are selected from the group consisting of $Cu^{2+}$, $Pt^{2+}$, $Pd^{2+}$, $Zn^{2+}$, $Y^{3+}$, $Sc^{3+}$, $Ce^{3+}$, $La^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and combinations thereof.

15. The method of claim 1, wherein said metal ions are lanthanide series metal ions.

16. The method of claim 15 wherein said lanthanide series metal ions are selected from the group consisting of $Ce^{3+}$, $La^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and combinations thereof.

17. The method of claim 1, wherein said metal ions are selected from the group consisting of $Cu^{2+}$, $Pt^{2+}$, $Pd^{2+}$, $Zn^{2+}$, and combinations thereof.

18. The method of claim 1, wherein said metal ions are selected from the group consisting of $Y^{3+}$, $Sc^{3+}$, and combinations thereof.

19. The method of claim 1, wherein said metal ion is $La^{3+}$.

20. The method of claim 1, wherein said organophosphorus compound is a pesticide.

21. The method of claim 1, wherein said organophosphorus compound is an insecticide.

22. The method of claim 1, wherein said organophosphorus compound is selected from paraoxon, fenitrothion, parathion, malathion, and $(C_2H_5O)_2P(O)$—S-(p-nitrophenyl).

23. The method of claim 1, wherein said organophosphorus compound is a chemical warfare agent.

24. The method of claim 23, wherein said organophosphorus compound is a G-agent.

25. The method of claim 23, wherein said organophosphorus compound is selected from the group consisting of $C_2H_5$—O—$P(O)(CH_3)$—$S(CH_2)_2N$(i-propyl)$_2$("VX") and (i-propyl)$CH_2$—O—$P(O)(CH_3)$—$S(CH_2)_2N(C_2H_5)_2$ ("Russian-VX").

26. The method of claim 23, wherein said organophosphorus compound is a nerve agent.

27. The method of claim 23, wherein said chemical warfare agent is combined with a polymer.

28. The method of claim 1, wherein said medium further comprises one or more ligands.

29. The method of claim 28, wherein said ligand is selected from the group consisting of 2,2'-bipyridyl, 1,10-phenanthryl, 2,9-dimethyiphenanthryl, crown ether, and 1,5,9-triazacyclododecyl.

30. The method of claim 28, wherein said ligand further comprises solid support material.

31. The method of claim 30, wherein said solid support material is selected from a polymer, silicate, aluminate, and combinations thereof.

32. The method of claim 1, wherein said medium is a solid.

33. The method of claim 1, wherein said medium is a solution.

34. The method of claim 33, wherein said solution is disposed on an applicatar.

35. The method of claim 1, wherein the metal ion: alkoxide ion ratio is in a range from 1:0.5 to 1:1.5.

36. The method of claim 1, wherein said organophosphorus compound is $C_2H_5$—O—P(O)(CN)—$N(CH_3)_2$ (Tabun or "GA").

37. The method of claim 1, wherein said organophosphorus compound is (i-propyl)-O—P(O)(F)$CH_3$, (Sarin or "GB").

38. The method of claim 1, wherein said organophosphorus compound is (t-butyl)$CH(CH_3)$—O—P(O)(F)$CH_3$ (Soman or "GD").

39. The method of claim 1, wherein said organophosphorus compound is cyclohexyl-O—P(O)(F)$CH_3$ ("GF").

40. The method of claim 23, wherein said organophosphorus compound is a v-agent.

41. The method of ciaim 1, wherein said neutral organophosphorus compound is a pesticide, insecticide, chemical warfare agent, or nerve agent; and wherein, through said alcoholysis reaction, said neutral organophosphorus compound is decomposed to a less toxic product.

42. The method of claim 1, wherein said neutral organophosphorus compound comprises at least one leaving group bonded to a phosphorus atom, said leaving group selected from the group consisting of halogens, alkanesulfonates, alkyl sulfates, and p-toluenesulfonates.

* * * * *

UNITED STATES PATENT AND TRADEMARK OFFICE

CERTIFICATE OF CORRECTION

PATENT NO. : 7,214,836 B2
APPLICATION NO. : 10/798880
DATED : May 8, 2007
INVENTOR(S) : R. Stanley Brown, Alexei A. Neverov and Josephine S. W. Tsang It is certified that error appears in the above-identified patent and that said Letters Patent is hereby corrected as shown below:

Column 38, Line 42
"Q,OQ," should be --Q, OQ,--;

Column 39, Line 24
"alkocyalkanol" should be --alkoxyalkanol--;

Column 40, Line 14
"dimethyiphenanthryl," should be --dimenthylphenanthryl--;

Column 40, Line 26
"applicatar." should be --applicator.--;

Column 40, Line 42
"ciaim" should be --claim--;

Signed and Sealed this

Twenty-seventh Day of May, 2008

JON W. DUDAS
*Director of the United States Patent and Trademark Office*